United States Patent
Abou Shousha et al.

(10) Patent No.: US 10,818,398 B2
(45) Date of Patent: Oct. 27, 2020

(54) SYSTEM AND METHOD FOR AI-BASED EYE CONDITION DETERMINATIONS

(71) Applicant: UNIVERSITY OF MIAMI, Miami, FL (US)

(72) Inventors: Mohamed Abou Shousha, Pembroke Pines, FL (US); Amr Saad Mohamed Elsawy, South Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 16/524,715

(22) Filed: Jul. 29, 2019

(65) Prior Publication Data

US 2020/0035362 A1      Jan. 30, 2020

Related U.S. Application Data

(63) Continuation-in-part of application No. 16/047,944, filed on Jul. 27, 2018, now Pat. No. 10,468,142.

(51) Int. Cl.
*G16H 50/20* (2018.01)
*G16H 50/50* (2018.01)
*A61B 3/00* (2006.01)
*G06T 7/00* (2017.01)
*G06N 3/04* (2006.01)

(52) U.S. Cl.
CPC .......... *G16H 50/20* (2018.01); *A61B 3/0025* (2013.01); *A61B 3/0058* (2013.01); *G06N 3/0454* (2013.01); *G06T 7/0016* (2013.01); *G16H 50/50* (2018.01); *G06T 2207/30041* (2013.01)

(58) Field of Classification Search
CPC ...... G16H 50/20; G16H 50/50; G06T 7/0016; G06T 2207/30041; G06N 3/0454; A61B 3/0058; A61B 3/0025
See application file for complete search history.

(56) References Cited

U.S. PATENT DOCUMENTS 10,121,059 B2 * 11/2018 Yoo ..................... G06K 9/00228
10,468,142 B1 * 11/2019 Abou Shousha .... A61B 3/0025
(Continued)

OTHER PUBLICATIONS

International Search Report and Written Opinion dated May 23, 2019, in corresponding PCT/US2019/016935 (12 pages).
(Continued)

*Primary Examiner* — John W Lee
(74) *Attorney, Agent, or Firm* — Pillsbury Winthrop Shaw Pittman LLP

(57) ABSTRACT

In some embodiments, a set of eye images related to a subject may be provided to a prediction model. A first prediction may be obtained via the prediction model, where the first prediction is derived from a first eye image and indicates whether an eye condition is present in the subject. A second prediction may be obtained via the prediction model, where the second prediction is derived from a second eye image and indicates that the eye condition is present in the subject. An aspect associated with the first prediction may be adjusted via the prediction model based on the second prediction's indication that the eye condition is present in the subject. One or more predictions related to at least one eye condition for the subject may be obtained from the prediction model, where the prediction model generates the predictions based on the adjustment of the first prediction.

18 Claims, 19 Drawing Sheets
(6 of 19 Drawing Sheet(s) Filed in Color)

(56) References Cited

U.S. PATENT DOCUMENTS

| | | | | |
|---|---|---|---|---|
| 2002/0036648 A1* | 3/2002 | Putilin | ............... | H04N 13/368 |
| | | | | 345/629 |
| 2005/0225724 A1* | 10/2005 | Klyce | ................... | A61B 3/107 |
| | | | | 351/212 |
| 2006/0210122 A1* | 9/2006 | Cleveland | .......... | G06K 9/00604 |
| | | | | 382/117 |
| 2010/0110374 A1* | 5/2010 | Raguin | ............... | G06K 9/0061 |
| | | | | 351/206 |
| 2011/0275931 A1 | 11/2011 | Debuc | | |
| 2012/0027275 A1* | 2/2012 | Fleming | ............... | G06F 19/321 |
| | | | | 382/128 |
| 2013/0128222 A1* | 5/2013 | Huang | ..................... | G06T 7/60 |
| | | | | 351/206 |
| 2017/0357879 A1* | 12/2017 | Odaibo | ................... | A61B 3/14 |

OTHER PUBLICATIONS

International Preliminary Report on Patentability dated Aug. 1, 2019, in corresponding PCT/US2018/013409 (14 pages).

Rabbani et al., "Obtaining Thickness Map of Corneal Layers Using the Optimal Alogrithm for Intracorneal Layer Segmentation," International Journal of Biomedical Imaging, vol. 2016, Article ID 1420230 (pp. 1-11).

Zhang et al., "A Novel Technique for Robust and Fast Segmentation of Corneal Layer Interfaces Based on Spectral-Domain Optical Coherence Tomography Imaging," IEEE Access, vol. 5, Jun. 8, 2017 (pp. 10352-10363).

Notice of Allowability dated Jul. 31, 2019, in corresponding U.S. Appl. No. 16/047,944 (9 pages).

Office Action dated Apr. 26, 2019, in corresponding U.S. Appl. No. 16/047,944 (13 pages).

* cited by examiner

| Image | Probability |
|---|---|
| 1 | 0.10 |
| 2 | 0.28 |
| 3 | 0.25 |
| 4 | 0.15 |
| 5 | 0.95 |
| 6 | 0.93 |
| 7 | 0.96 |
| 8 | 0.23 |
| 9 | 0.26 |
| 10 | 0.24 |
| ... | ... |

FIG. 6

| Eye | Probability |
|---|---|
| Left Eye | 0.92 |
| Right Eye | 0.43.5 |

FIG. 7

AI Results – Subclinical Case

MANIFEST REFRACTION

|  | Right | Left |
|---|---|---|
| Sphere | -8.75 | -9.00 |
| Cylinder | +1.75 | +1.75 |
| Axis | 090 | 090 |
| Distance Visual Acuity | 20/20 | 20/20 |

FIG. 9

AI Results – Left Eye

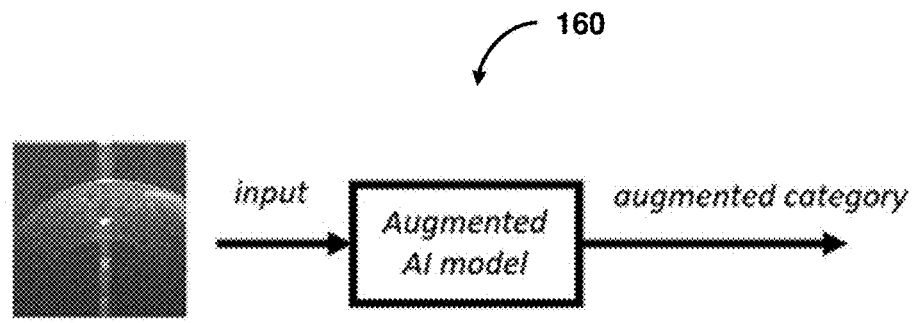
FIG. 19A
| disease | severity | risk | action | treatment | Category |
|---------|----------|------|--------|-----------|----------|
| ... | ... | ... | ... | ... | ... |
| $d_k$ | $s_k$ | $r_k$ | $a_k$ | $t_k$ | $c_k$ |
| ... | ... | ... | ... | ... | ... |
FIG. 19B
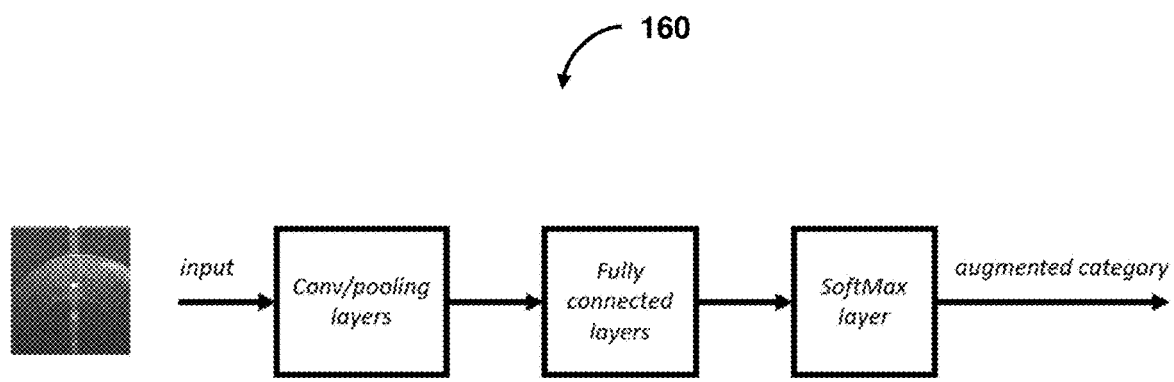
FIG. 19C

SYSTEM AND METHOD FOR AI-BASED EYE CONDITION DETERMINATIONS

RELATED APPLICATION(S)

This application is a continuation-in-part of U.S. application Ser. No. 16/047,944, entitled "Artificial Intelligence-Based System and Methods for Corneal Diagnosis," filed Jul. 27, 2018, which is hereby incorporated by reference herein in its entirety.

STATEMENT OF GOVERNMENT SUPPORT

This invention was made with government support under Grant No. K23EY026118 awarded by the National Institute of Health. The government has certain rights in the invention.

FIELD OF THE INVENTION

The invention relates to facilitating determinations related to eye conditions or treatments thereof, including, for example, providing diagnosis or evaluation of corneal or other eye conditions (or other conditions) via a neural network or other prediction model.

BACKGROUND OF THE INVENTION

Although scanning and diagnostic systems for detecting eye conditions exist, many such systems involve invasive procedures and/or tests that are not representative of patient symptoms, including such systems to scan or analyze characteristics of aqueous deficiency, evaporative dry eye syndrome (DES), corneal ectasia, corneal limbal stem cell deficiency, keratoplasty graft rejection episode or failure, Fuchs' dystrophy, or other conditions. As an example, while confocal microscopy can be used to diagnose DES, it is a time-consuming procedure that requires contact with the ocular surface, making it difficult to incorporate into everyday clinics and limits its use as a research tool. Tear film osmolarity is another technique used to diagnose DES, but it is also invasive and time consuming.

In addition, given the large number of corneal transplants performed annually, it is important to non-invasively detect eye conditions of a donor cornea (e.g., Fuchs' dystrophy or other conditions) prior to transplanting the cornea. Slit-lamp examination is one technique used to detect such eye conditions, but this technique offers only limited magnification and often misses detection of potential subclinical rejection episodes. Other techniques (e.g., endothelial cell count using specular microscopy, central cornea thickness measurements, etc.) lack sufficient reproducibility or sensitivity, limiting their usefulness in the diagnosis of mild cases. The wide range of normal corneal thickness also complicates their usefulness for diagnosis of mild cases (e.g., mild corneal graft rejection, edema, ectasia, etc.). As an example, there is significant overlap between normal thin corneas and early ectasia patients, making it difficult to detect ectasia in its early stages. These and other drawbacks exist.

SUMMARY OF THE INVENTION

Aspects of the invention relate to methods, apparatuses, and/or systems for facilitating determinations related to eye conditions or treatments thereof via a neural network or other prediction model.

In some embodiments, one or more predictions related to at least one eye condition for a subject may be obtained via a prediction model based on a set of eye images related to the subject. In some embodiments, the prediction model may be configured to generate the predictions based on the set of eye images, and the generated predictions may be obtained from the prediction model. As an example, the prediction model may be configured to (i) take, as input, eye images of the subject; (ii) obtain a first prediction related to an eye condition, (iii) obtain a second prediction related to the eye condition; and (iv) adjust an aspect associated with the first prediction based on an aspect associated with the second prediction, where the first prediction is derived from a first eye image of the eye images, and the second prediction is derived from a second eye image of the eye images. As another example, the prediction model may be a neural network including at least one input layer, at least one hidden layer, and at least one output layer. In a further use case, the input layer of the neural network may be configured to take, as input, the eye images of the subject. The hidden layer of the neural network may be configured to obtain the foregoing predictions and adjust the aspect of the first prediction based on the aspect associated with the second prediction. The output layer may be configured to output the adjusted first prediction or other final predictions.

In some embodiments, one or more predictions may be adjusted based on a clustering of predictions. As an example, a clustering of predictions may be performed based on eye locations associated with the predictions, and certain predictions may be adjusted based on such clustering. As an example, subsets of a set of eye images provided to a prediction model may respectively represent a different portion of an eye of a subject, such as a different microlayer of the eye, a different sublayer within a microlayer of the eye, or other different portion of the eye. A prediction derived from an eye image may be associated with a location of the eye that corresponds to the eye portion represented by the eye image. Predictions derived from eye images may be clustered together based on a determination that the predictions are associated with eye locations close in proximity with one another. As an example, if there are a cluster of predictions indicating that the subject has keratoconus, the confidence scores associated with those predictions may be increased to account for characteristics of keratoconus being isolated in one or more regions of the cornea in its early stages. In this way, for example, the clustering-based predictions can provide better accuracy for detection of keratoconus or other eye conditions with such attributes.

In some embodiments, a prediction related to presence of an eye condition in one eye of the subject may be adjusted based on a prediction related to presence of the eye condition (or other eye condition) in the other eye of the subject. As an example, some conditions are typically bilateral but asymmetrical. Presence of a condition in one eye makes the other eye more likely to have the same condition, but with different severity or in a subclinical form. As such, in one use case, a weight or probability of a prediction indicating that an eye condition is present in one eye of the subject may be increased based on a prediction indicating that the eye condition is present in the other eye of the subject. Thus, for example, the foregoing can provide better accuracy for the detection of eye conditions with such bilateral attributes.

Various other aspects, features, and advantages of the invention will be apparent through the detailed description of the invention and the drawings attached hereto. It is also to be understood that both the foregoing general description and the following detailed description are exemplary and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 2A is an OCT B-scan, FIG. 2B is a thickness map showing total cornea thickness, and FIG. 2C is a bullseye map showing total cornea thickness, in accordance with one or more embodiments.

FIG. 6 illustrates predicted probabilities that an eye condition is present, where the predicted probabilities are derived from respective images, in accordance with one or more embodiments.

FIG. 7 illustrates predicted probabilities that an eye condition is present with respect to a subject's left and right eyes, in accordance with one or more embodiments.

FIG. 9 illustrates data derived from a manifest refraction, in accordance with one or more embodiments.

FIG. 19A illustrates a schematic diagram that includes an augmented category AI model, in accordance with one or more embodiments.

FIG. 19B illustrates a table representing augmented categories for an augmented category AI model, in accordance with one or more embodiments.

FIG. 19C illustrates a schematic diagram that includes an augmented category AI model, in accordance with one or more embodiments.

DETAILED DESCRIPTION OF THE INVENTION

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

Figure 1A:
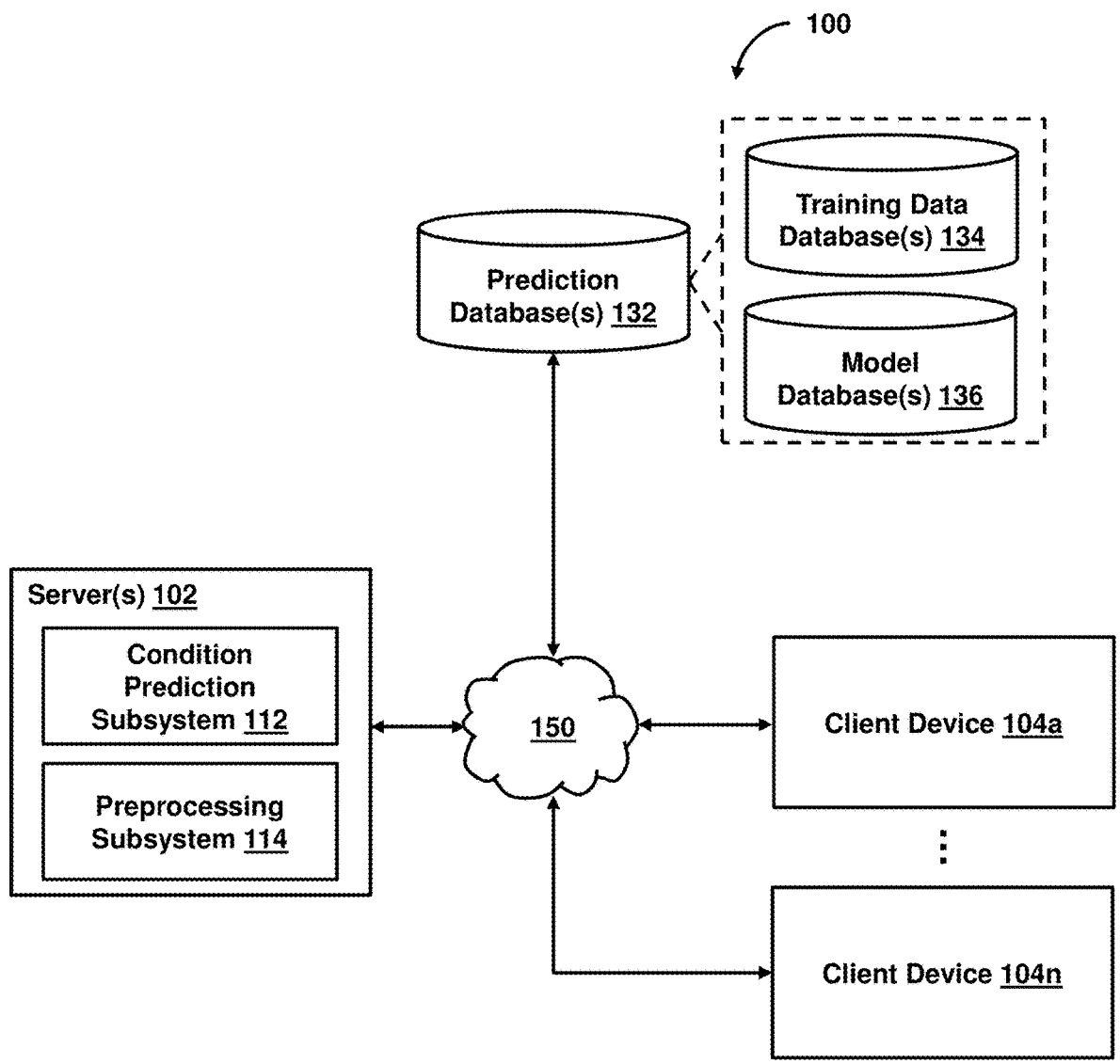
FIG. 1A illustrates a system for facilitating determinations related to eye conditions or treatments thereof, in accordance with one or more embodiments.

FIG. 1A shows a system 100 for facilitating determinations related to eye conditions or treatments thereof, in accordance with one or more embodiments. As shown in FIG. 1A, system 100 may include server(s) 102, client device 104 (or client devices 104a-104n), or other components. Server 102 may include condition prediction subsystem 112, preprocessing subsystem 114, or other components. By way of example, client device 104 may include a desktop computer, a notebook computer, a tablet computer, a smartphone, a wearable device, or other client device. Users may, for instance, utilize one or more client devices 104 to interact with one another, one or more servers, or other components of system 100.

It should be noted that, while one or more operations are described herein as being performed by particular components of client device 104, those operations may, in some embodiments, be performed by other components of client device 104 or other components of system 100. As an example, while one or more operations are described herein as being performed by components of client device 104, those operations may, in some embodiments, be performed by components of server 102. It should also be noted that, while one or more operations are described herein as being performed by particular components of server 102, those operations may, in some embodiments, be performed by other components of server 102 or other components of system 100. As an example, while one or more operations are described herein as being performed by components of server 102, those operations may, in some embodiments, be performed by components of client device 104. It should further be noted that, although some embodiments are described herein with respect to machine learning models, other prediction models (e.g., statistical models or other analytics models) may be used in lieu of or in addition to machine learning models in other embodiments (e.g., a statistical model replacing a machine learning model and a non-statistical model replacing a non-machine-learning model in one or more embodiments).

In some embodiments, system 100 may generate one or more predictions related to at least one eye condition of the subject based on one or more images related to the subject's eyes. As an example, the eye images may include one or more images of a retina of at least one of the subject's eyes (e.g., the overall retina or a portion thereof), one or more images of a cornea of at least one of the subject's eyes (e.g., the overall cornea or a portion thereof), or other eye images. As another example, the predictions include one or more predictions related to at least one of corneal ectasia, Keratoconus, corneal graft rejection episode and failure, dry eye syndrome (DES), Fuchs' dystrophy, corneal limbal stem cell deficiency, cataract, glaucoma, or other eye condition. As a further example, the predictions may include one or more predictions indicating (i) whether any of the foregoing conditions is present in the subject or will likely be present in the subject in the future (e.g., currently present in an eye of the subject, the respective risks of such conditions developing in the eye of the subject if corrective treatment or action is taken or not taken, etc.), (ii) severities of such conditions predicted to be present in the subject or severity score associated therewith, (iii) treatments or actions to be taken with respect to such conditions, (iv) probabilities that the eye of the subject will respond favorably or unfavorably to such treatments or actions, or (v) other information.

It should be noted that, although some embodiments are described herein with respect to use of corneal images, other images related to a condition of the subject (e.g., other eye images related at least one eye condition of the subject or other images derived from scans of the subject) may be used in lieu of or in addition to corneal images.

In some embodiments, one or more prediction models may be used to facilitate determinations related to eye conditions or other operations. In some embodiments, the prediction models may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

Figure 1B:
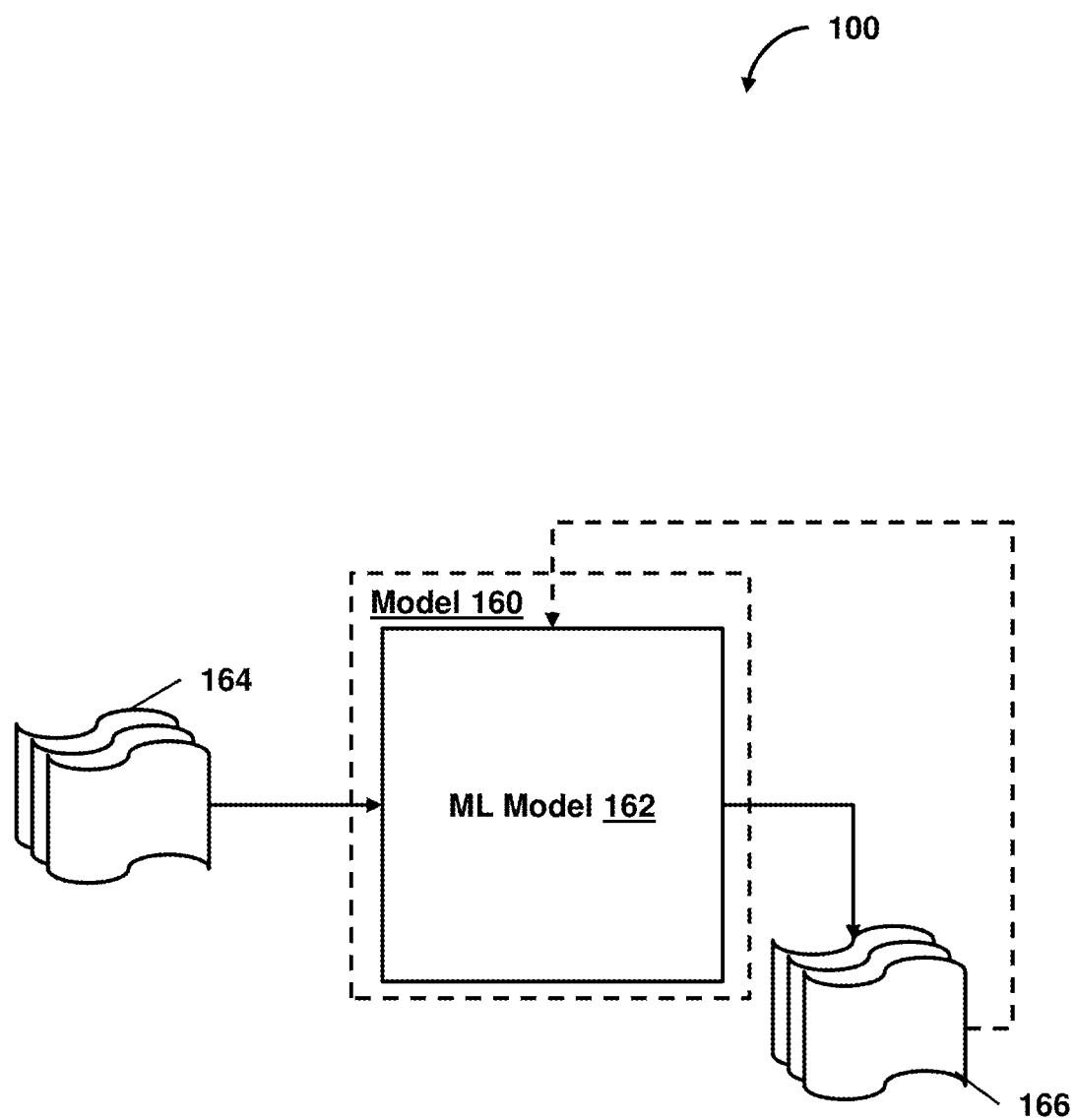
FIG. 1B illustrates a system implementing a machine learning model to facilitate determinations related to eye conditions or treatments thereof, in accordance with one or more embodiments.
Figure 2A:
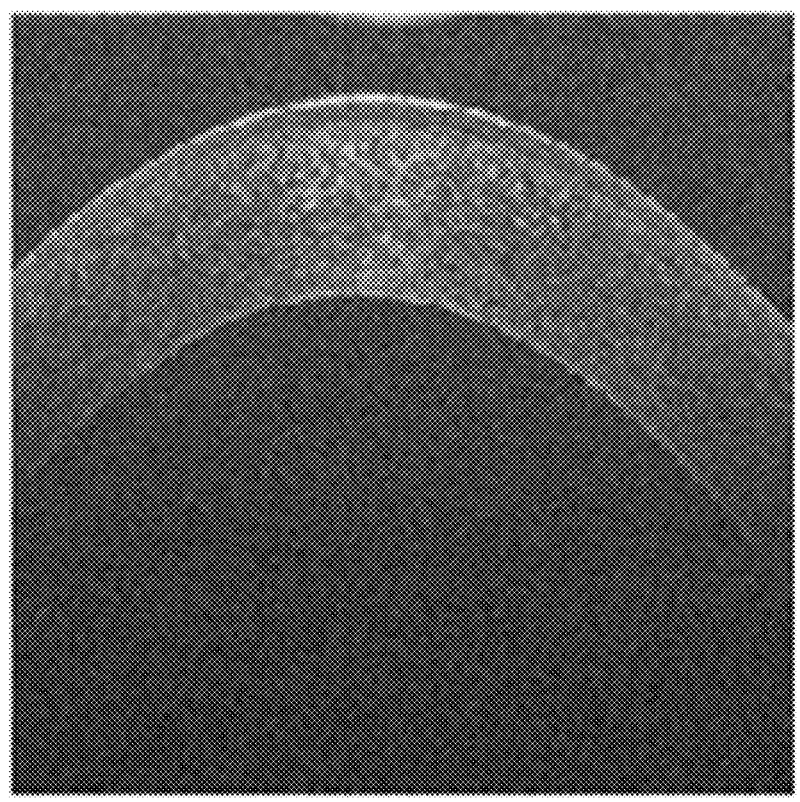
FIGS. 2A-2C illustrate examples of input data, where
Figure 2B:
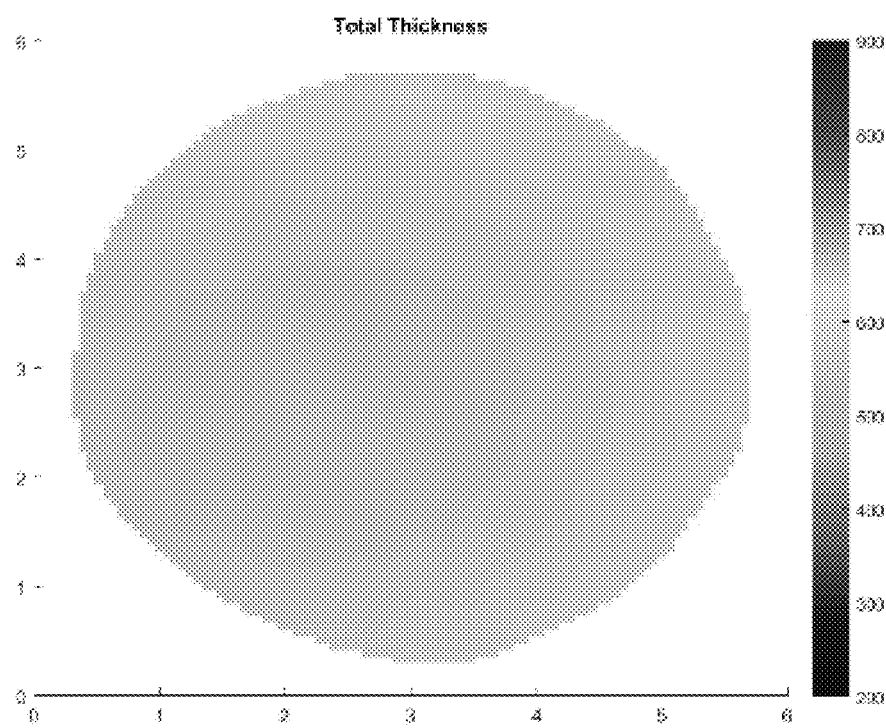
Figure 2C:
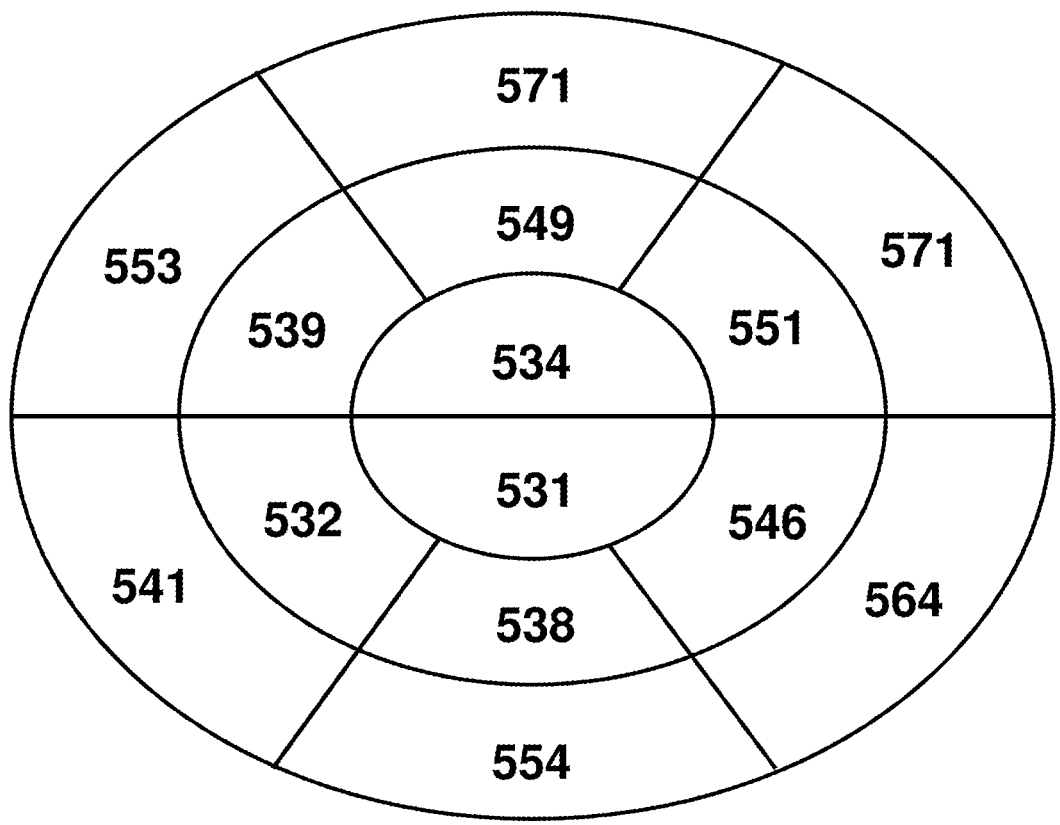

As an example, with respect to FIG. 1B, the AI model 160 may include machine learning model 162 configured to take inputs 164 and provide outputs 166. In one use case, outputs 166 may be fed back to machine learning model 162 as input to train machine learning model 162 (e.g., alone or in conjunction with user indications of the accuracy of outputs 166, labels associated with the inputs, or with other reference feedback information). In another use case, machine learning model 162 may update its configurations (e.g., weights, biases, or other parameters) based on its assessment of its prediction (e.g., outputs 166) and reference feedback information (e.g., user indication of accuracy, reference labels, or other information). In another use case, where machine learning model 162 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the prediction model may be trained to generate better predictions.

In some embodiments, system 100 may provide multiple frames of the same image cut (e.g., the same image cut of a microlayer of an eye) from an eye scan to a prediction model to train the prediction model. As an example, the multiple frames may include multiple raw frames of the same image cut obtained from the eye scan, where each frame of the multiple raw frames of the same image cut includes different noise patterns from other frames of the multiple raw frames. Thus, for example, such training based on the different noise patterns may enable the prediction model to be more robust to noise.

In some embodiments, system 100 may utilize a prediction model for preprocessing of an initial set of images and another prediction model to process the preprocessed set of images to generate one or more predictions. As an example, the preprocessing prediction model may remove problematic or low-quality images from the set of images (to be provided to the other prediction model). In one scenario, the preprocessing prediction model may remove images from the set of images that the preprocessing prediction model determines (i) are not properly aligned (e.g., not properly centered with respect to the subject's cornea), (ii) has too much noise, or (iii) has other issues that would reduce the accuracy of the other prediction model's predictions. As another example, the preprocessing prediction model may perform modifications of one or more images of the set of images, such as denoising an image, removing artifacts from an image, aligning an image (e.g., centering an image with respect the subject's cornea), or performing other modifications to increase the accuracy of the other prediction model's predictions. In one use case, the preprocessing prediction model may align images of an initial set of eye images related to the subject to obtain a set of aligned images and provide aligned images to the other prediction model. The other prediction model may process the aligned images and output one or more predictions based on the aligned images.

In some embodiments, system 100 may provide a set of eye images related to a subject to a prediction model and obtain, via the prediction model, one or more predictions related to at least one eye condition for the subject. As an example, the prediction model may be configured to generate the predictions based on the set of eye images, and system 100 may obtain the generated predictions from the prediction model. In one use case, the prediction model is configured to (i) take, as input, eye images of the subject; (ii) obtain a first prediction related to an eye condition, (iii) obtain a second prediction related to the eye condition; and (iv) adjust an aspect associated with the first prediction based on an aspect associated with the second prediction, where the first prediction is derived from a first eye image of the eye images, and the second prediction is derived from a second eye image of the eye images. In another use case, the prediction model may be a neural network including at least one input layer, at least one hidden layer, and at least one output layer. In a further use case, the input layer of the neural network may be configured to take, as input, the eye images of the subject. The hidden layer of the neural network may be configured to obtain the foregoing predictions and adjust the aspect of the first prediction based on the aspect associated with the second prediction. The output layer may be configured to output the adjusted first prediction or other final predictions (e.g., the second prediction or an adjusted version thereof, a further modified version of the first prediction, etc.).

In some embodiments, one or more predictions may be adjusted based on a clustering of predictions. As an example, a clustering of predictions may be performed based on eye locations associated with the predictions, and certain predictions may be adjusted based on such clustering. In some embodiments, system 100 may perform such adjustments via one or more prediction models. As an example, subsets of a set of eye images provided to a prediction model may respectively represent a different portion of an eye of a subject, such as a different microlayer of the eye, a different sublayer within a microlayer of the eye, or other different portion of the eye. A prediction derived from an eye image (e.g., one of the images provided as input to the prediction model) may be associated with a location of the eye that corresponds to the eye portion represented by the eye image. Predictions derived from eye images may be clustered together based on a determination that the predictions are associated with eye locations close in proximity with one another. In one use case, weights or probabilities of certain predictions (e.g., predictions indicating presence of a particular eye condition) may be increased based on those predictions being within the same cluster or being associated with eye locations close in proximity with one another. As an example, if there are a cluster of predictions indicating that the subject has keratoconus, the confidence scores (e.g., probabilities or other scores) associated with those predictions may be increased to account for characteristics of keratoconus being isolated in one or more regions of the cornea in its early stages. In this way, for example, the clustering-based predictions can provide better accuracy for detection of keratoconus or other eye conditions with such attributes.

In some embodiments, a prediction related to presence of an eye condition in one eye of the subject may be adjusted based on a prediction related to presence of the eye condition (or other eye condition) in the other eye of the subject. In some embodiments, system 100 may perform such adjustments via one or more prediction models. As an example, some conditions are typically bilateral but asymmetrical (e.g., keratoconus, Fuchs' dystrophy, etc.). Presence of a condition in one eye makes the other eye more likely to have the same condition, but with different severity or in a subclinical form. As such, in one use case, a weight or probability of a prediction indicating that an eye condition is present in one eye of the subject may be increased based on a prediction indicating that the eye condition is present in the other eye of the subject. Thus, for example, the foregoing can provide better accuracy for the detection of eye conditions with such bilateral attributes.

In some embodiments, condition prediction subsystem 112 may provide a set of eye images related to a subject as input to a prediction model and obtain, via the prediction model, one or more predictions related to at least one eye condition for the subject. As an example, the prediction model may generate the predictions based on the set of eye images, and condition prediction subsystem 112 may obtain the predictions from the prediction model. In some embodiments, one or more B-scan images (or B-scans), one or more thickness maps (e.g., indicating thickness of one or more microlayers of an eye of the subject) or other mapping data, or other image data may be provided as input to the prediction model. As an example, the prediction model may be configured to take, as input, the B-scans and the thickness maps and generate the predictions based on the B-scans and the thickness maps. Other inputs (e.g., provided to the prediction model and on which the predictions may be based) may include demographics data (e.g., age, gender, ethnicity, past medical history, family history, or occupation, etc.) medical data (e.g., corneal curvature, central corneal thickness, eye pressures, visual fields, or visual acuity related to the subject, a condition of the subject's other eye, the prior condition of state of the imaged eye, etc.), or other data.

For example, the AI model 160 (or one or more submodels thereof) may take an input (e.g., OCT B-scans, thickness maps, bullseye maps, heat maps, color coded maps, or color images of the cornea and anterior segment) and then output a prediction. Additionally or alternatively, the input data may include curvature maps, topography maps, tomography maps, elevation maps, or other maps. For example, the input data may include a map of the cornea representing contours or curvature of the cornea or one or more of its layers. In a further example, the input data includes a map representing relative contour, curvature or elevation of the cornea or one or more of its layers relative to each other or relative to a defined sphere, surface, or curve. These maps may be produced by application of mapping techniques to images such as OCT images or other high-definition images. In various embodiments, map generation may be performed according to the systems and methods disclosed in U.S. patent application Ser. No. 15/868,856, titled "Method and System for Three-Dimensional Thickness Mapping of Corneal Micro-Layers and Corneal Diagnosis," filed Jan. 11, 2018, the contents of which are hereby incorporated herein by reference.

In one example, the maps may be of the overall cornea or one or more of its layers. Graft rejection of the cornea, for example, may be marked by general global thickening of the cornea and more substantial thickening of the endothelial layer/Descemet's membrane relative to the rest of the cornea. Thus, input data may include total cornea thickness maps and/or thickness maps of each layer. Keratoconus is another example where a specific pattern of thickening of the epithelium at the area where the stroma and Bowman's layers may be thinned. These patterns of relative thickening and thinning are difficult to represent with an index but may be detected by a prediction model (e.g., the AI model 160) that looks at the thickness data of all the layers at the same time and detects such patterns.

In some embodiments, the input data includes a temporal sequence of images taken at different times that capture how the cornea state has evolved. Such input data may be used with respect to prediction models trained to predict effective treatment, effectiveness of current or future treatments, recovery time, condition, or other predictions. In one example, the system 100 includes utilizing a recurrent neural network for modeling time series by representing the sequence of images into a time series. In further examples, the network architecture for the recurrent neural network is modified to process series of images instead of series of points. This is useful for the prediction of disease progression because the disease progression is a temporal process.

In some embodiments, a prediction model may be configured to generate multiple predictions related to an eye condition based on eye images of an input set and adjust an aspect associated with one of the predictions based on an aspect associated with one or more other ones of the predictions. As an example, each prediction of the multiple predictions may be derived from a different eye image of the eye images of the input set. Aspects associated with a prediction may include the predicted information, a weight or probability associated with the prediction, a probability associated with the prediction, a portion of an eye (to which the prediction corresponds) or other eye location associated with the prediction, or other aspects. The predicted information may include (i) whether any eye condition is present in the subject or will likely be present in the subject in the future (e.g., currently present in an eye of the subject, the respective risks of such conditions developing in the eye of the subject if corrective treatment or action is taken or not taken, etc.), (ii) severities of such conditions predicted to be present in the subject or severity score associated therewith, (iii) treatments or actions to be taken with respect to such conditions, (iv) probabilities that the eye of the subject will respond favorably or unfavorably to such treatments or actions, or (v) other information.

In one use case, where the prediction model includes a neural network, the neural network may include a plurality of layers, such as one or more input layers, hidden layers, and output layers. At least one input layer of the neural network may be configured to take eye images as input to the neural network. At least one hidden layer of the neural network may be configured to (i) obtain a first prediction related to an eye condition, (ii) obtain a second prediction related to the eye condition, and (iii) adjust an aspect associated with the first prediction based on an aspect associated with the second prediction. As an example, the hidden layer may obtain the predictions from one or more other hidden layers of the neural network, and the other hidden layers may derive the predictions from the eye images of the input set (e.g., where the first prediction is derived from a first eye image, the second prediction is derived from a second eye image, etc.). In another use case, at least one output layer of the neural network may be configured to perform the foregoing operations of the hidden layer.

In some embodiments, condition prediction subsystem 112 may provide a set of eye images (related to a subject) as input to a prediction model, where the input set includes eye images representing different portions of one or more eyes of the subject, such as a different microlayer of an eye, a different sublayer within a microlayer of the eye, or other different eye portion of the eye. As an example, microlayers of an eye may include the epithelium, the basal epithelium, the Bowman's layer, the Descemet's membrane, the endothelium, or other microlayers. In some embodiments, the prediction model may generate intermediate predictions based on the eye images of the input set such that (i) a first intermediate prediction is based on a first eye image representing a first eye portion, (ii) a second intermediate prediction is based on a second eye image representing a second eye portion, (iii) a third intermediate prediction is based on a third eye image representing a third eye portion, and (iv) so on, where each of the first, second, and third eye portions are different portions of an eye of the subject. Each of the intermediate predictions may be associated with an eye location corresponding to the respective eye portion (e.g., a name or other identifier for the respective eye portion or other information indicating a location of the respective eye portion). As an example, the first intermediate prediction may be associated with a first eye location corresponding to the first eye portion, the second intermediate prediction may be associated with a second eye location corresponding to the second eye portion, the third intermediate prediction may be associated with a third eye location corresponding to the third eye portion, and so on.

In one use case, where the prediction model includes a neural network, the neural network may include a plurality of layers, such as one or more input layers, hidden layers, and output layers. At least one input layer of the neural network may be configured to take eye images as input to the neural network. At least one hidden layer of the neural network may be configured to (i) obtain the first intermediate prediction, (ii) obtain the second intermediate prediction, and (iii) adjust an aspect associated with the first intermediate prediction based on an aspect associated with the second intermediate prediction. As an example, the hidden layer may obtain the intermediate predictions from one or more other hidden layers of the neural network, and the other hidden layers may derive the intermediate predictions from the eye images of the input set (e.g., where the first intermediate prediction is derived from a first eye image, the second intermediate prediction is derived from a second eye image, etc.). In another use case, at least one output layer of the neural network may be configured to perform the foregoing operations of the hidden layer.

In some embodiments, weights or probabilities associated with one or more predictions may be adjusted based on one or more other predictions and aspects associated with the other predictions. As an example, a weight or probability associated with a first prediction may be adjusted based on a second prediction and an eye location associated with the second prediction. In some embodiments, a prediction model may generate intermediate predictions based on eye images of an input set such that (i) a first intermediate prediction is based on a first eye image representing a first eye portion and (ii) a second intermediate prediction is based on a second eye image representing a second eye portion. The prediction model may be configured to adjust a weight or probability associated with at least one of the first or second intermediate predictions based on a distance between (i) a first eye location associated with the first intermediate prediction (and corresponding to the first eye portion) and (ii) a second eye location associated with the second intermediate prediction (and corresponding to the second eye portion).

In some embodiments, where the first and second intermediate predictions' associated eye locations are close in proximity to one another, the prediction model may be configured to increase the weights or probabilities associated with the first or second intermediate predictions. As an example, the prediction model may increase the weights or probabilities associated with the first or second intermediate predictions based on (i) the first and second intermediate prediction indicating that the same eye condition is present in an eye of the subject and (ii) the first eye location associated with the first intermediate prediction being close in proximity to the second eye location associated with the second intermediate prediction. As a further example, the first and second eye locations may be determined to be close in proximity with one another based on the first and second eye locations being within a threshold distance from one another (e.g., a predetermined threshold distance or other threshold distance).

In some embodiments, one or more predictions may be adjusted based on a clustering of predictions. As an example, the prediction model may use one or more clustering techniques to determine clusters of predictions such that each of the clusters includes predictions (i) associated with eye locations close in proximity to one another, (ii) associated with eye locations within a threshold distance of an eye location associated with the cluster, (iii) associated with eye locations on a layer associated with the cluster (e.g., a microlayer associated with the cluster), or (iv) that have other attributes associated with the cluster. As another example, the prediction model may increase the weights or probabilities associated with the first or second intermediate predictions based on (i) the first and second intermediate prediction indicating that the same eye condition is present in an eye of the subject and (ii) the first and second intermediate predictions being associated with the same cluster. As indicated above, such clustering-based adjustments (along with the foregoing eye-location-based adjustments related to the predictions) in some embodiments enable attributes of certain eye conditions (e.g., characteristics of keratoconus being isolated in one or more regions of the cornea in its early stages) to be taken into account, thereby providing better accuracy for detection of such eye conditions.

In one use case, with respect to FIG. 6, the prediction model may generate predictions for one of the patient's eyes (e.g., intermediate predictions) based on eye images 1-*n* (e.g., images 1-10) of that eye, where the predictions specify probabilities of a patient having a particular eye condition (e.g., keratoconus or other eye condition). As shown, although the predictions derived from images 5-7 specify high probabilities of the patient having the eye condition (e.g., 95%, 93%, and 96%), the other predictions derived from images 1-4 and 8-10 specify low probabilities of the patient having the eye condition. If, for example, there are only the 10 predictions, and the weights used to average the predictions (or its probabilities) are equal for each prediction, then the prediction model may output a final prediction that the eye condition is not present in the patient's eye (e.g., based on the weighted average being 43.5%).

In another use case, however, if images 5-7 represent portions of the patient's eye that are close in proximity to one another (e.g., areas of the same microlayers that are close in proximity to one another), the prediction model may be configured to increase the weights of the predictions derived from images 5-7 based on (i) a determination of the close proximity of the portions represented by images 5-7 and (ii) the predictions derived from images 5-7 specifying probabilities satisfying a threshold related to presence of the eye condition (e.g., 70% or greater, 80% or greater, or other probability that the eye condition is present in the subject's eye). Additionally, or alternatively, the prediction model may be configured to decrease the weights of the predictions derived from the other images (e.g., images 1-4 and 8-10) based on (i) the close proximity of the portions represented by images 5-7 and the predictions derived from images 5-7 specifying probabilities satisfying the presence threshold and (ii) the predictions derived from the other images specifying probabilities not satisfying the presence threshold (e.g., lower than the presence threshold). As an example, if there are only the 10 predictions, and the prediction model increases the weight of each of the predictions derived from images 5-7 to five times greater than the weight of each of the other predictions, then the prediction model may output a final prediction that the eye condition is present in the patient's eye (e.g., based on the weighted average being 71.4%).

In a further use case, even if images 1-4 represent portions of the patient's eye that are close in proximity to one another (e.g., areas of the same microlayers that are close in proximity to one another), the prediction model may be configured not to increase the weights of the predictions derived from images 1-4 (or at least configured not to increase the weights of such predictions to a greater extent than the increase of the weights of predictions associated with images 5-7). In this way, for example, the prediction model may be configured to take into account attributes of certain conditions being isolations in one or more regions of the eye (e.g., characteristics of keratoconus being isolated in one or more regions of the cornea in its early stages) without allowing the close proximity of predictions indicating lack of a presence of such conditions to influence (or overinfluence) the final predictions of whether such conditions are present in the patient's eye.

Figure 8:
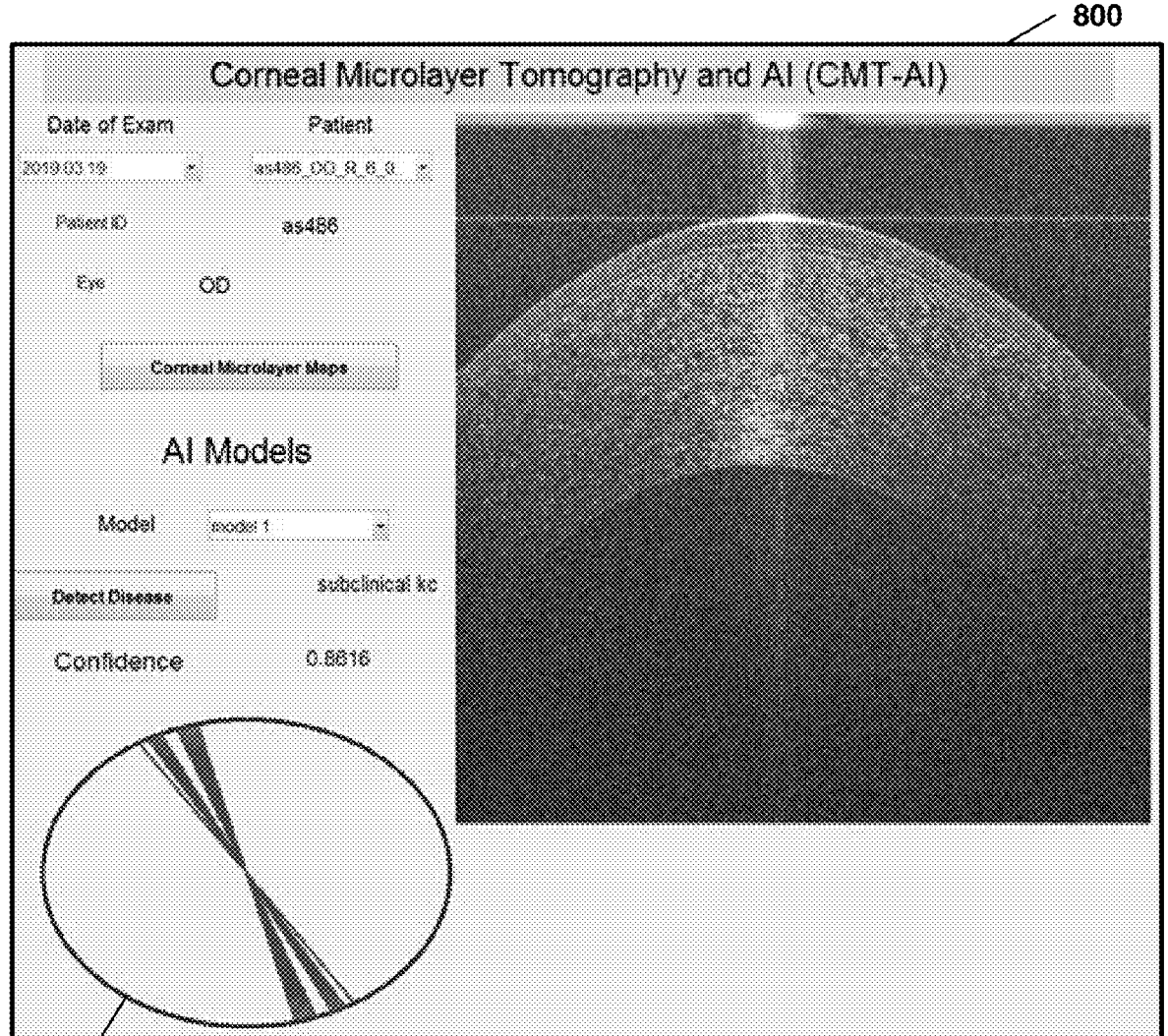
FIG. 8 illustrates results derived from an AI model indicating the presence of a subclinical case of an eye disease, in accordance with one or more embodiments.

In one use case, with respect to FIG. 8, a subclinical case of an eye disease (e.g., keratoconus) are often missed by current standard of card tests. In the use case shown in FIG. 8, when a prediction model processed 200 frames from an eye scan of a subject's eye, the prediction model generated an intermediate prediction of no keratoconus for over 90% of the frames (see blank/lighter area in visualization 802 of user interface 800) and an intermediate prediction of keratoconus for less than 10% of the frames (see red/darker area in visualization 802 of user interface 800). As such, if all of the predictions were given the same weight and averaged, the final prediction would have been a prediction that keratoconus is not present in the subject's eye. However, because most of the intermediate predictions of keratoconus were associated with eye locations that are close in proximity to one another (e.g., within a threshold distance from one another, in the same clusters, etc.), the prediction model increased the weights of the predicted probabilities for the intermediate predictions of keratoconus (e.g., and without increasing the weights of the other predicted probabilities, decreasing the weights of the other predicted probabilities, etc.). Based on the updated weights, the prediction model generated a final predicted probability of 86.16% that keratoconus is present in the subject's eye (see confidence of 0.8616 in user interface 800). As indicated on user interface 800, an indication that the keratoconus is in a subclinical stage (or other early disease stage) may be provided on the user interface 200. As an example, the prediction model may generate the subclinical stage indication as an additional prediction. In some embodiments, the sub clinical indication may be generated based on the number of frames associated with intermediate predictions of keratoconus failing to satisfy a threshold amount of predictions (e.g., 20% of frames, 10% of frames, or other threshold amount).

Figure 10A:
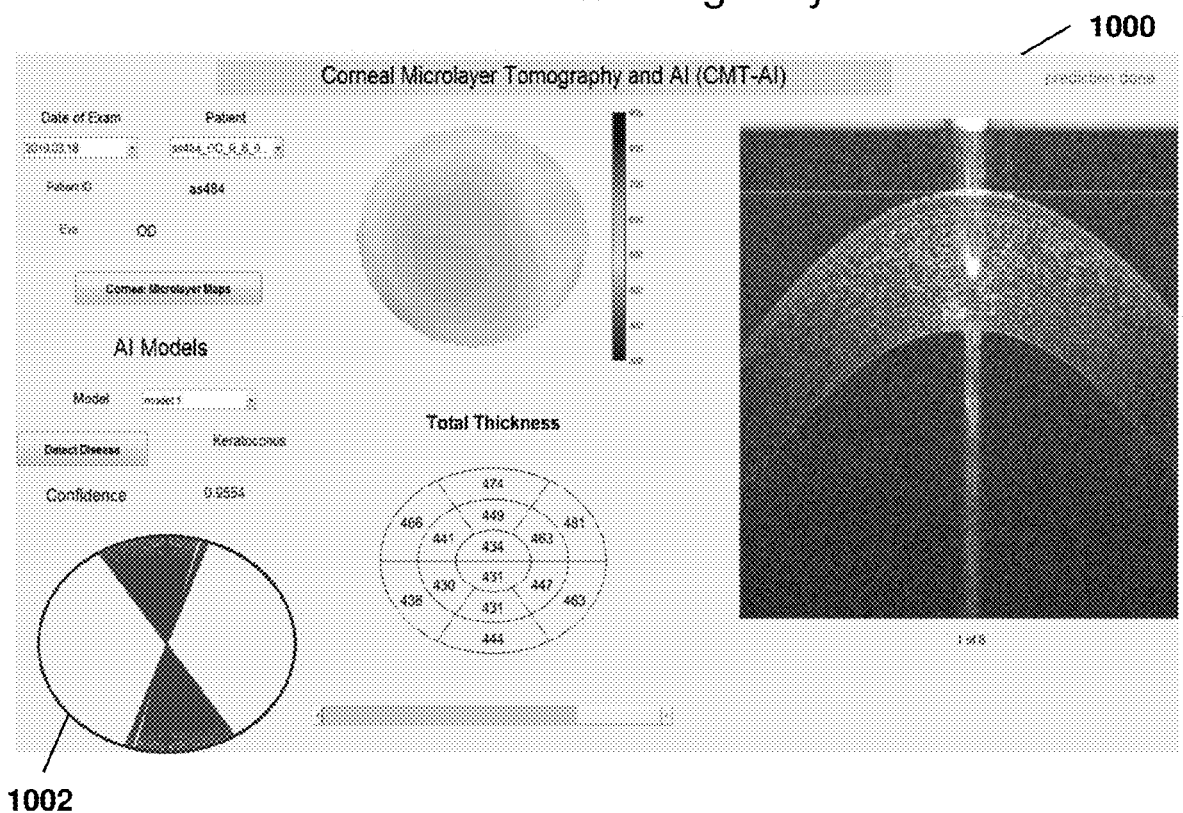
FIGS. 10A-10B illustrate results derived from an AI model indicating the presence of an eye disease in both of a patient's eyes, in accordance with one or more embodiments.
Figure 10A:
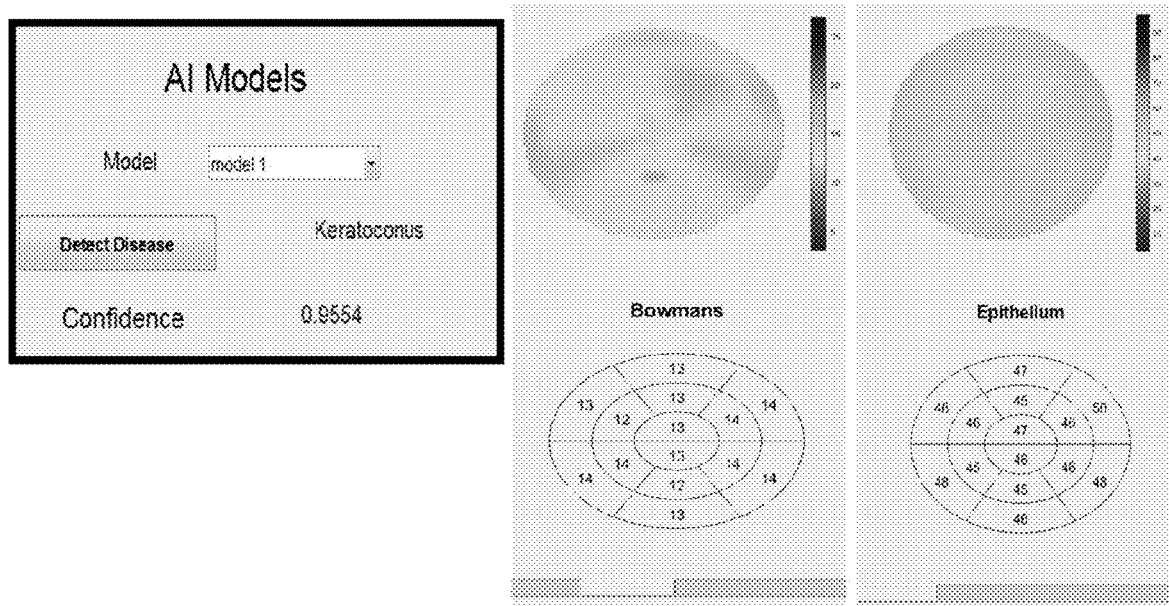
Figure 10B:
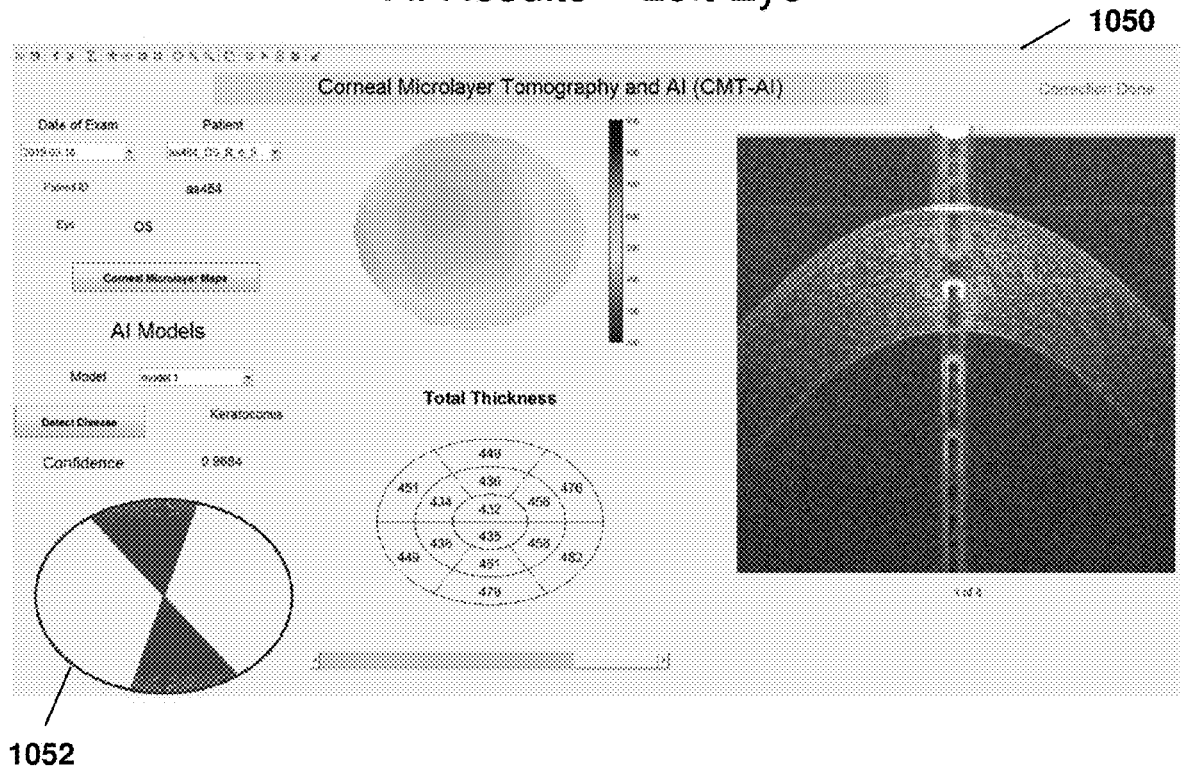
Figure 10B:
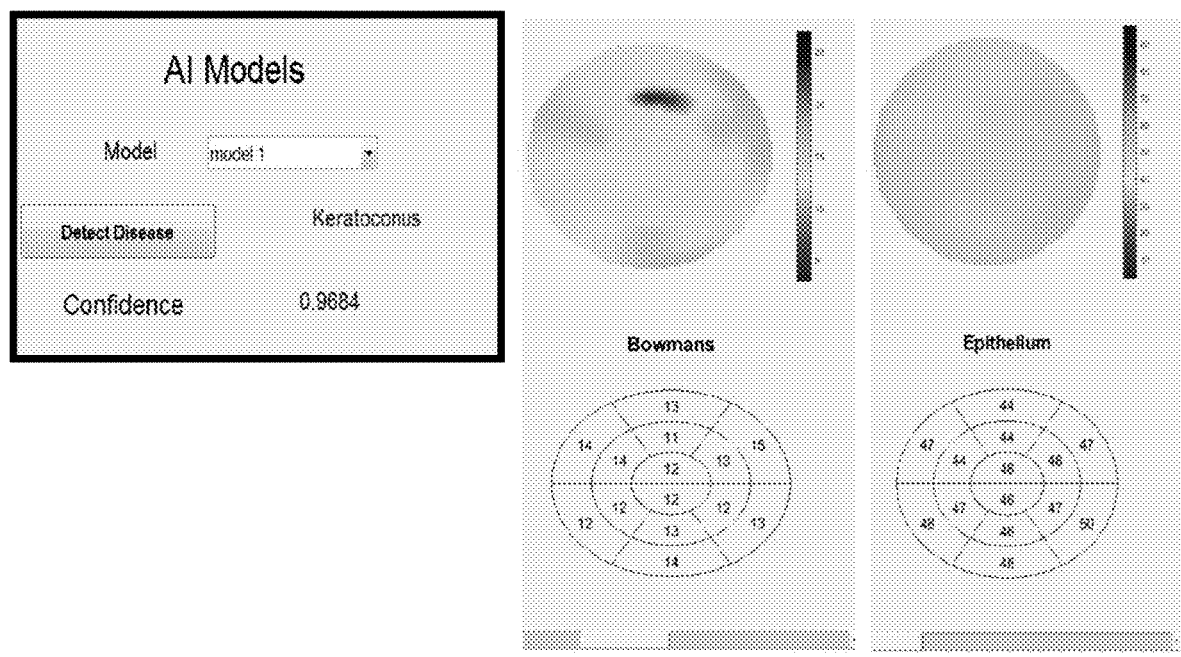

In another use case, with respect to FIGS. 9, 10A, and 10B, the prediction model generated a prediction that a 27-year-old female patient with very little astigmatism (as indicated in FIG. 9 by the data derived from a manifest refraction) has keratoconus in both eyes even though it is uncommon for patients with a small amount of astigmatism to have keratoconus, and prior testing techniques most likely would have produced a diagnosis of no keratoconus. As indicated in FIGS. 10A and 10B, when the prediction model processed 200 frames from an eye scan for each of the patient's eyes, the prediction model generated an intermediate prediction of no keratoconus for close to 70% of the frames (see blank/lighter area in visualizations 1002 and 1052 of user interfaces 1000 and 1050) and an intermediate prediction of keratoconus for close to 30% of the frames (see red/darker area in visualizations 1002 and 1052 of user interfaces 1000 and 1050). If all of the predictions were given the same weight and averaged, the final prediction for each eye would have been a prediction that keratoconus is not present in either of the subject's eyes. However, because most of the intermediate predictions of keratoconus were associated with eye locations that are close in proximity to one another, the prediction model increased the weights of the predicted probabilities for the intermediate predictions of keratoconus. Based on the updated weights, the prediction model generated a final predicted probability of 95.54% that keratoconus is present in the subject's right eye (see confidence of 0.9554 in user interface 1000) and a final predicted probability of 96.84% that keratoconus is present in the subject's left eye (see confidence of 0.9684 in user interface 1050).

In some embodiments, condition prediction subsystem 112 may provide a set of eye images (related to a subject) as input to a prediction model, where the input set includes one or more eye images representing one eye of the subject and one or more eye images representing another eye of the subject. In some embodiments, the prediction model may generate intermediate predictions based on the eye images of the input set such that a first intermediate prediction is based on one or more eye images representing a first eye of the subject and a second intermediate prediction is based on one or more eye images representing a second eye of the subject. In some embodiments, at least one of the intermediate predictions may be adjusted based on at least another one of the intermediate predictions. As an example, the first intermediate prediction may be related to presence of an eye condition in one eye of the subject, and the second intermediate prediction may be related to presence of the eye condition (or other eye condition) in the other eye of the subject. The first intermediate prediction may be adjusted based on the second intermediate prediction. In some embodiments, the prediction model may increase a weight or probability associated with the first intermediate prediction (that an eye condition is present in one eye of the subject) may be increased based on the second intermediate prediction indicating that the eye condition is present in the other eye of the subject. As an example, some conditions are typically bilateral but asymmetrical (e.g., keratoconus, Fuchs' dystrophy, etc.). Presence of a condition in one eye makes the other eye more likely to have the same condition, but with a different severity or in a subclinical form. Thus, for example, the foregoing can provide better accuracy for the detection of eye conditions with such bilateral attributes.

In one use case, with respect to FIG. 7, the prediction model may generate a first prediction for a patient's left eye (e.g., a first intermediate prediction based on one or more eye images of the left eye) and a second prediction for the patient's right eye (a first intermediate prediction based on one or more images of the right eye), where the predictions specify probabilities of the patient's respective eyes having a particular eye condition (e.g., keratoconus or other eye condition). As shown, for example, the first prediction may be a probability of 92% that the left eye has the eye condition, and the second prediction may be a probability of 43.5% that the right eye has the eye condition. In one scenario the prediction model may increase the second prediction's probability of 43.5% to a higher probability based on the first prediction's probability of 92% satisfying a probability threshold (e.g., 70% or greater, 80% or greater, or other probability that the right eye has the eye condition).

In another scenario, the first prediction's probability of 92% may be used as a parameter to calculate the increase to the second prediction's probability. In a further scenario, the second prediction's probability of 43.5% may be derived from a set of immediate probabilities, such as those predicted from images of the right eye (e.g., probabilities associated with images 1-10 of FIG. 6). Based on the first prediction's probability satisfying the probability threshold, the prediction model may increase weights associated with the intermediate probabilities that indicate presence of the eye condition in the right eye (e.g., the intermediate probabilities that satisfies the probability threshold). As an example, where the intermediate probabilities are those associated with images 1-10 of FIG. 6, the prediction model may increase the weights of each of the intermediate probabilities derived from images 5-7 to five times greater than the weight of each of the other probabilities. If there are only the 10 intermediate probabilities, then the second prediction's probability of 43.5% may be increased to the weighted average of 71.4% that the eye condition is present in the right eye. If the second prediction's increased probability satisfies the probability threshold, the prediction model may provide an output that the eye condition is present in both the left and right eyes. Additionally, or alternatively, the output may specify the first prediction's probability, the second prediction's probability subsequent to the increase, the second prediction's probability prior to the increase, or other information.

In some embodiments, where the prediction model includes a neural network, the neural network may include a plurality of layers, such as one or more input layers, hidden layers, and output layers. At least one input layer of the neural network may be configured to take eye images as input to the neural network. At least one hidden layer of the neural network may be configured to (i) obtain the first intermediate prediction (related to presence of an eye condition in one eye of the subject), (ii) obtain the second intermediate prediction (indicating that the eye condition is present in another eye of the subject), and (iii) adjust the first intermediate prediction (e.g., by increasing the weight to indicate presence of the eye condition) based on the second intermediate prediction indicating that the eye condition is present in the other eye. As an example, the hidden layer may obtain the intermediate predictions from one or more other hidden layers of the neural network, and the other hidden layers may derive the intermediate predictions from the eye images of the input set (e.g., where the first intermediate prediction is derived from an eye image of a first eye of the subject, the second intermediate prediction is derived from an eye image of a second eye of the subject, etc.).

In some embodiments, the presence of an eye condition in one eye may be incorporated as a weight that can be multiplied by the probability of the diagnosis in the other eye. Weight may be determined by incidence data or via a prediction model that determines the bilateral probability from existing training data. In some instances, patient data such as demographics may similarly be incorporated. In some embodiments, recurrent neural networks or Bayesian networks may be used to model such data.

In various embodiments, the AI model 160 takes as input images of both eyes (e.g., B-scans or other images), mapping-related image data (e.g., thickness maps, heat maps, bullseye maps, structural maps, etc.), or other image data. The output probabilities of each data input may be used to adjust the output probabilities of one or more of the other probabilities. As described herein, the AI model 160 may include multiple submodels. The submodels may be integrated into one or more submodels. In some embodiments, multiple submodels may be combined by feed forward of input, scores, or predictions into subsequent submodels. In one embodiment, multiple submodels may be combined by integration of various layers, blocks of layers, or combinations of layers or blocks. Inputs may include multiple image types or data forms, which may include patient data such as demographics data. Multiple inputs may be input at various stages of the AI model 160. For example, additional data inputs may be input as weights within fully connected layers or applied as multipliers of scores of one or more submodels. In one example, the AI model takes as input images of both eyes (e.g., one or more B-scans of each eye and/or one or more heat maps of one or both eyes). The AI model may predict a disease in one eye which may increase the probability of the disease in the other eye. As an example, based on a predicted probability that the disease is present in a first eye, the AI model may increase the predicted probability of the disease in the second eye by multiplying the predicted probability for the second eye by one or more weights or other parameters (e.g., predetermined or fixed weights or parameters, weights or parameters that are dependent on the predicted probability for the first eye, etc.).

In some embodiments, preprocessing subsystem 114 may provide an initial set of eye images (related to a subject) to a prediction model to obtain a preprocessed set of eye images (e.g., to be provided to another prediction model to generate one or more predictions). As an example, the preprocessing prediction model may remove problematic or low-quality images from the set of images (to be provided to the other prediction model). In one scenario, the preprocessing prediction model may remove images from the set of images that the preprocessing prediction model determines (i) are not properly aligned (e.g., not properly centered with respect to the subject's cornea), (ii) has too much noise, or (iii) has other issues that would reduce the accuracy of the other prediction model's predictions. As another example, the preprocessing prediction model may perform modifications of one or more images of the set of images, such as denoising an image, removing artifacts from an image, aligning an image (e.g., centering an image with respect to the subject's cornea), cropping or scaling an image (e.g., as part of the alignment of the image), or performing other modifications to increase the accuracy of the other prediction model's predictions.

Figure 3A:
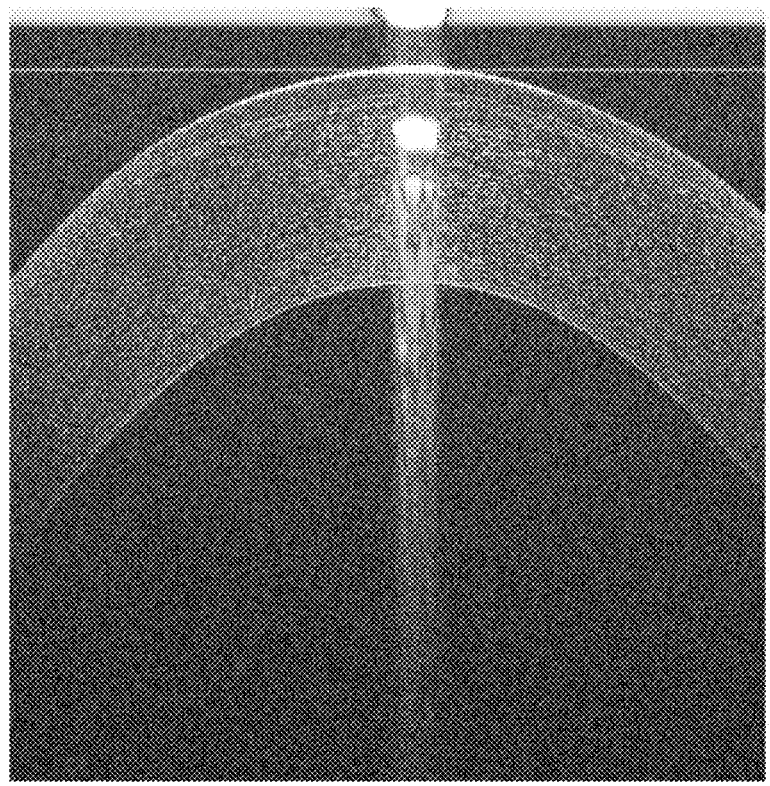
FIGS. 3A-3B illustrate an input image and the output image of a preprocessing operation that removes artifacts of the input image, in accordance with one or more embodiments.
Figure 3B:
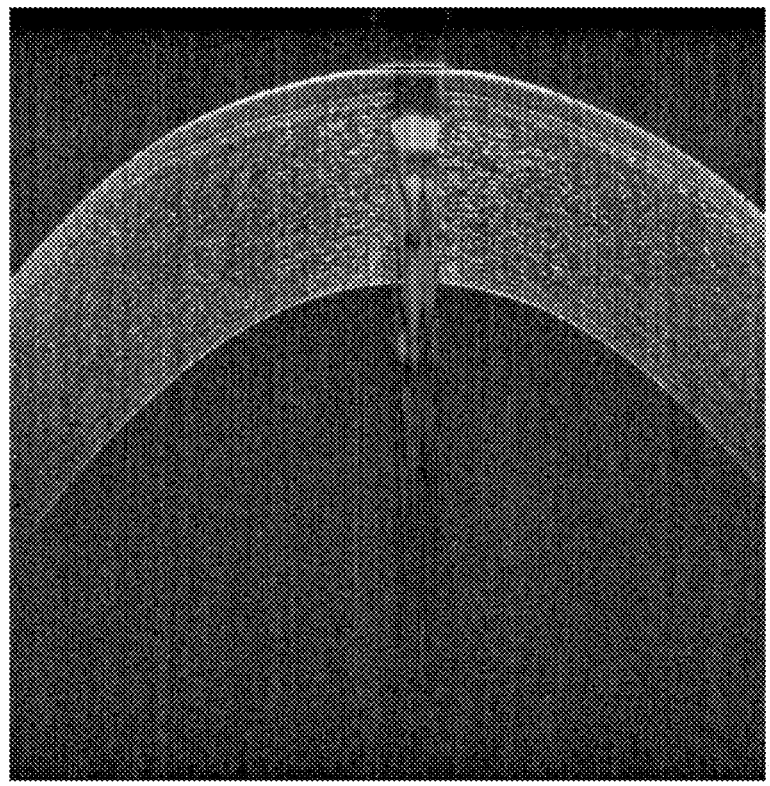

In one use case, the preprocessing prediction model may be trained to identify artifacts in an eye image that do not commonly exist in other eye images and remove such artifacts from the eye image. As an example, anterior segment OCT images often may have distinct artifacts that do not commonly exist in OCT images of another type (e.g., specular reflections, horizontal artifacts, etc.). Such artifacts may be identified and removed by the preprocessing prediction model to improve the accuracy of the other prediction model that processes the preprocessed OCT images and outputs one or more predictions based on the preprocessed OCT images. As an example, the image shown in FIG. 3A is a raw B-scan image of the anterior segment of an eye that includes vertical and horizontal artifacts. FIG. 3B shows the B-scan image of FIG. 3A after the removal of artifacts via preprocessing techniques.

In another use case, the preprocessing prediction model may be trained to align images of an initial set of eye images related to the subject to obtain a set of aligned images and provide aligned images to the other prediction model. As an example, the alignment may be performed such that the aligned images are more aligned with respect to a given reference (e.g., a center of the subject's cornea, another reference point of the subject's eye, etc.). The other prediction model may process the aligned images and output one or more predictions based on the aligned images. In one use case, the preprocessing prediction model may perform one or more transformations (e.g., rotation, reflection, translation, resizing, etc.), cropping, or other techniques on an image to center the image with respect to a center of the subject's cornea.

In some embodiments, condition prediction subsystem 112 or preprocessing subsystem 114 may provide multiple frames of a same image cut from an eye scan to a prediction model (e.g., for training or other purposes). The multiple frames may include multiple raw frames (of the same image cut from the eye scan), preprocessed frames derived from the raw frames (e.g., frames preprocessed to have less noise, to be more aligned with respect to a given reference, etc., as compared to the raw frames), or other frames of the same image cut from the eye scan. In some embodiments, where the prediction model is a preprocessing prediction model, the prediction model may perform alignment of the multiple frames, removal of artifacts from the multiple frames, identify one or more of the multiple frames to be excluded from use as input images to another prediction model, or other operations. In some embodiments, the prediction model may generate at least one prediction related to at least one eye condition based on the multiple frames of the same image cut. As an example, by using different frames of the same image cut, the cuts may include different noise patterns (e.g., due to noise being random when each frame is captured), and such training based on the different noise patterns may enable the prediction model to be more robust to noise.

In some embodiments, input image data includes multiple images that capture a current state of a patient's cornea or anterior segment. For example, the input image data may include multiple B-scan images taken along a same cut or multiple cuts of the cornea or anterior segment. In this or another example, the input image data may include a sequence of images as a temporal sequence. The input data may include multiple B-scan images comprising one or more images of the patient's left and right corneas or anterior segment. As indicated above, the accuracy of the system 100 may be improved utilizing multiple B-scans of the same eye. For example, the system 100 may calculate a probability of a diagnosis for each single B-scan and then calculate a mean of the probabilities from the total B-scans of the same eye. The averaging may be taken from independent predictions generated for each scan.

As indicated above, the prediction model may be trained to generate a prediction. In various embodiments, the prediction may include a set of scores. As an example, the output may include a set of scores, where each score is generated by a corresponding node in the output layer. The set of scores may include classification or category scores corresponding to particular category probabilities, such as disease (or other condition), which may correspond to probability of the presence of a discrete category or a continuous scale value score, for example. The set of scores may be referred to as condition scores. The condition scores may correspond to likelihood of a particular condition of the cornea or anterior segment. Condition scores may correspond to a risk, severity, action, or treatment outcome related to one or more particular conditions of the cornea or anterior segment. For example, the prediction may associate each output node with a score which can be normalized using a SoftMax layer to give the likelihood of each category. In one embodiment, the set of scores is related to some medical condition. In these or other embodiments, each score may correspond to a prediction of risk of some future health event, severity of a medical condition, disease progression, an action or treatment, or an outcome of a treatment. In one example, the set of scores includes a set of condition scores, where at least one of the scores represents a likelihood of a medical condition-related to a corneal or anterior segment condition. In one example, the set of scores includes a corresponding score representing the likelihood of the severity of a corneal or anterior segment condition. In another example, the set of scores includes a corresponding score representing the likelihood that the patient will develop the corneal or anterior segment condition in the future. In still another example, the set of scores include a corresponding score representing the likelihood that the patient will respond favorably or unfavorably to treatment for the corneal or anterior segment condition. In yet another example, the set of scores includes a corresponding score assisting or guiding a physician decision to utilize a specific treatment technique for the corneal or anterior segment condition. For example, the score may indicate positive or negative treatment techniques or success rates related to techniques applied to eyes having similar features or attributes. In still yet another example, the set of scores include a corresponding score representing the likelihood that the patient's corneal or anterior segment condition will get worse or improve in the future. In various embodiments, the set of scores includes one or more corresponding scores selected from those representing the likelihood of the severity of the corneal or anterior segment condition, representing a severity score of the corneal or anterior segment condition, representing the likelihood that the patient will develop the corneal or anterior segment condition in the future, representing the likelihood that the patient will respond favorably or unfavorably to treatment for the corneal or anterior segment condition, assisting or guiding a physician decision to utilize a specific treatment technique for the corneal or anterior segment condition, or representing the likelihood that the patient's corneal or anterior segment condition will get worse or improve in the future.

Figure 4:
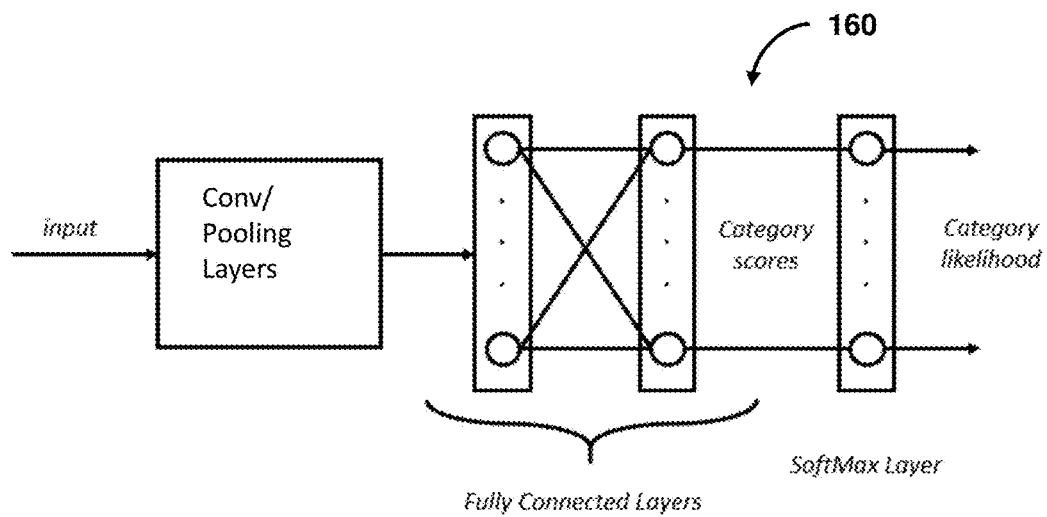
FIGS. 4-5 each illustrates an AI model for outputting a prediction related to an eye of a subject, in accordance with one or more embodiments.

FIG. 4 schematically illustrates the AI model 160 for generating predictions related to the cornea or anterior segment of the eye, in accordance with one or more embodiments. The AI model 160 may include an input layer, a plurality of convolutional and pooling layers, a plurality of fully connected layers, and an output layer comprising a SoftMax layer. The AI model 160 may include various arrangements of convolutional layers, pooling layers, fully connected layers, an output layer comprising one or more normalization layers and/or classification layers, which may include a regression layer, as well as other layers. In the illustrated embodiment, the AI model 160 includes a set of convoluted and pooling layers followed by a set of fully connected layers and an output layer. The output layer includes a normalization and/or classification layer, which includes a SoftMax layer in the illustrated embodiment. In one embodiment, the classification layer includes a classical classifier such as a discriminant analysis or support vector machine (SVM). In some embodiments, the output layer may further include instead or in addition to an SVM or SoftMax, a classifier layer comprising a binary classifier. After converting an image into a set of features through convolutional layers, these features may be used with other classifiers which may be part of the same or a different output layer block.

In the depicted operation, the network takes input data (e.g., an image) and processes the input data through a set of layers to generate the final output comprising a likelihood for each category or class to which the network is trained. The output may include a set of scores, which in one embodiment may be a single score. The class or category may include cornea or anterior segment conditions, treatments, severity classes, risk degrees or classes, treatment outcome classes or progression, prognosis, or other network goal or target. More specifically, the input data is processed through a set of convolutional layers and pooling layers, such as max pooling layers. The values or activations (which may be referred to as activation or feature maps) from the last layer of the set of convolutional and pooling layers are passed to a set of fully connected layers for higher level processing (e.g., more global processing related to a classification task). In the final fully connected layer, each node represents a class or category. The network associates each output node with a score, which can be normalized using a classification layer, such as a SoftMax layer in this example, to give the likelihood of each category. In some embodiments, each score may comprise a prediction of a risk of some future health event. Only outer nodes and connections are illustrated, but the fully connected and classification layer may include additional nodes. Nodes are not illustrated for the convolution and pooling layers; however, these layers will typically include much larger numbers of nodes than fully connected layers. In some embodiments, the AI model 160 may be further configured to provide augmented predictions from a single model prediction. For example, as described in more detail below, the AI model 160 may include a model that outputs a condition prediction and one or more additional predictions, which may be related to the condition prediction, such as one or more of risk, severity, progression, action, treatment, or prognosis.

Figure 5:
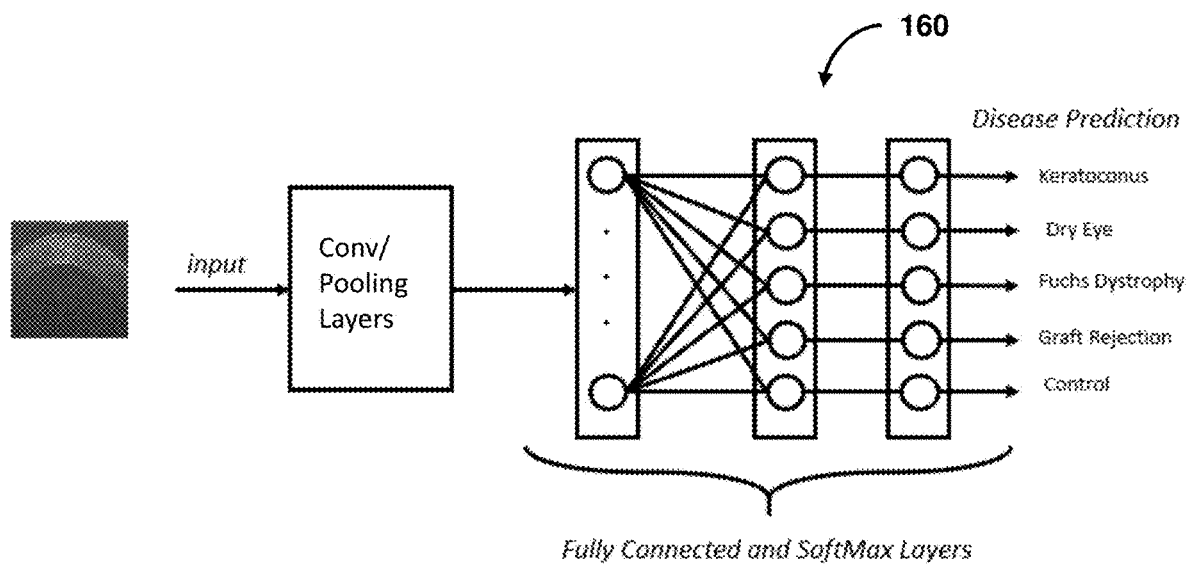

FIG. 5 schematically illustrates the AI model 160 for predicting a condition of the cornea or anterior segment of the eye, in accordance with one or more embodiments. As an example, the AI model 160 is trained to obtain and process one or more input images to generate one or more predictions.

The AI model 160 may include various arrangements of convolutional layers, pooling layers, fully connected layers, an output layer comprising one or more normalization layers and/or classification layers, which may include a regression layer, as well as other layers. In the illustrated embodiment, the AI model 160 includes a set of convoluted and pooling layers followed by a set of fully connected layers and an output layer. The output layer includes a normalization and/or classification layer, which includes a SoftMax layer in the illustrated embodiment. In one embodiment, the classification layer includes a classical classifier such as a discriminant analysis or support vector machine (SVM). In some embodiments, the output layer may further include instead or in addition to an SVM or SoftMax, a classifier layer comprising a binary classifier. After converting an image into a set of features through convolutional layers, these features may be used with other classifiers which may be part of the same or a different output layer block. Thus, various embodiments may combine aspects from different AI modeling methodologies with one or more convolutional neural networks comprising convolutional/pooling layer blocks (cony/pooling layers). It will be appreciated that cony/pooling layer blocks in any embodiment described herein may include other layers therebetween or prior to the fully connected layer block such as one or more ReLU layer.

The output layer of the AI model 160 receives the output generated by the last fully connected layer and generates the model output. The model output may include a set of scores, where each score is generated by a corresponding node in the output layer. The set of scores include condition scores. Generally, the set of condition scores is specific to a medical condition that the AI model 160 has been trained to predict, such as a condition of the cornea or anterior segment of the eye. For example, the AI model 160 output in FIG. 5 is specific to a medical condition, such as a condition, represented by the nodes of the final fully connected layer and the nodes of the output layer, which in this embodiment includes a SoftMax layer. More specifically, the AI model 160 has been trained to predict corneal or anterior segment conditions, such as keratoconus, dry eye, Fuchs' dystrophy, graft rejection episode or failure, and glaucoma.

The AI model 160 may be trained to predict multiple medical conditions and multiple combinations of those medical conditions. For example, in one embodiment, the set of condition scores may represent the likelihood that the patient has some corneal or anterior segment condition selected from corneal ectasia (such as keratoconus), keratoplasty graft rejection episode and failure, corneal graft rejection, aqueous deficiency and evaporative dry eye syndrome (DES), Fuchs' dystrophy, corneal limbal stem cell deficiency, cataract, or glaucoma. In other embodiments, each score may comprise a prediction of a risk of some future health event.

Thus, the AI model 160 may be configured to provide multiple diagnoses, such as up to two diagnoses, for the same eye, if a second diagnosis is present. For example, the probability of a diagnosis is calculated and if a second diagnosis has a probability above a threshold then that second diagnosis may also be provided. In some embodiments, the output layer of the AI model 160 may include a binary classifier that is executed to detect which of one or more classes, such as conditions, to include in the prediction or diagnosis. For example, the diagnosis could be keratoconus with dry eye. In some embodiments, the AI model 160 may be configured to provide more than two diagnoses when present.

In some embodiments, the AI model 160 may be further configured to provide augmented predictions from a single model prediction. For example, as described in more detail below, the AI model 160 may include a model that outputs a condition prediction and one or more additional predictions, which may be related to the condition prediction, such as one or more of risk, severity, risk, progression, action, treatment, or prognosis.

As introduced above, the system 100 may be configured to include an AI model 160 having an efficient design. The AI model 160, for example, may include simple categories, such as single prediction member, and/or compound or complex categories that include multiple prediction members in a single category (e.g., augmented categories). In one example, in the training of the AI model 160, a category that represents cases which have multiple conditions as a separate case may be added. For example, the AI model 160 may include members that overlap with those in a single member category, such as in the example above. In other embodiments, there may be no member overlap. In one example, all categories are compound or complex. Thus, the system 100 may introduce the concept of simple categories and compound, complex, or augmented categories.

In a further embodiment, the set of condition scores includes one or more corresponding scores selected from those representing the likelihood of the severity of the corneal or anterior segment condition, representing a severity score of the corneal or anterior segment condition, representing the likelihood that the patient will develop the corneal or anterior segment condition in the future, representing the likelihood that the patient will respond favorably or unfavorably to treatment for the corneal or anterior segment condition, assisting or guiding a physician decision to utilize a specific treatment technique for the corneal or anterior segment condition, or representing the likelihood that the patient's corneal or anterior segment condition will get worse or improve in the future.

In some embodiments, with respect to FIG. 5, the AI model 160 may additionally or alternatively be configured for predicting a severity of a condition of the cornea or anterior segment of the eye. As an example, the AI model 160 may be trained to predict a level of severity for one or more particular conditions of the cornea or anterior segment of the eye. The output may include a discrete value or category corresponding to the level of severity of a cornea or anterior segment condition. As another example, the AI model 160 may predict the likelihood that the patient's cornea has some medical condition and predict the condition level. The AI model 160 may include simple categories, such as single prediction member, and/or compound or complex categories that include multiple prediction members in a single category (e.g., augmented categories). In some embodiments, the predictions may be made through separate AI models. For example, after making an initial prediction identifying a condition, the system 100 may process the input data through a second AI model 160 (e.g., CNN) specific to the condition identified to generate a predicted severity.

In some embodiments, the predictions may be made through a single AI model 160 comprising a CNN, where the probability score is used to correlate a severity. For example, a first threshold probability may lead to a predicted condition and additional thresholds in the probability score may be set to indicate severity as the probability score increases. In a further example, a first output node outputs to a second output node, such as when the output value is above a predefined threshold. The second output node may be specific to a condition implicated by the threshold value. In one embodiment, the second output node applies a weighted algorithm to the output value to determine a severity level of a condition. In another example, the predictions may be made in a joint CNN or a CNN that diverges or converges. For example, the AI model 160 may include separate sets of fully connected layers that fully connect to common convoluted, pooling, or fully connected layers. In a further example, the CNN may include additional convoluted and pooling layers after diverging into separate fully connected layers. The CNN may therefore include multiple sets of fully connected and output layers configured to perform separate classification tasks from the same initial input data diverted along separate processing paths. Multiple networks or sub-models may similarly be combined or converged into one network. In some embodiments, converging, diverging or combined networks may be trained jointly. For example, training may include defining a global loss function (e.g., error function) based on an output of the individual networks and tuning the networks accordingly.

In some embodiments, with respect to FIG. 5, the AI model 160 may additionally or alternatively be configured for predicting a severity score of a condition of the cornea or anterior segment of the eye. Thus, in contrast to the AI model that predicts a level of severity of a medical condition, the AI model 160 is trained to represent severity by a score instead of a discrete value. This may be useful when a continuous scale value is wanted from the system 100.

As an example, the AI model 160 has been trained to predict a severity for one or more particular conditions of the cornea or anterior segment of the eye. In operation, the input layer receives the data input, which is then processed through the convolutional and pooling layers before the processing is passed to the fully connected layers. After being processed through the fully connected layers, the node of the output layer receives the output activation values generated by the nodes of the last fully connected layer. The output layer may comprise an output node that then processes the activation values to generate a model output comprising a severity score, which is a continuous score corresponding to the level of severity of the patient's cornea. The output layer may comprise a regression layer comprising the output node. In some embodiments, the output layer may comprise a normalization layer to conform an activation value to an output score in a desired range. In one embodiment, the output layer comprises a SoftMax layer configured to normalize one or a combination of the activation values to calculate a normalized output score comprising the prediction score.

In some embodiments, with respect to FIG. 5, the AI model 160 may additionally or alternatively be configured for generating a risk prediction, such as a prediction of the progression of a cornea or anterior segment condition. The AI model 160 is configured to output a discrete value or category corresponding to the predicted risk for a patient's cornea. In one example, the AI model 160 configured to output risk predictions with respect to keratoconus may include values representing a patient's risk or likelihood of having a progressive course or stable course. In another example, the AI model 160 configured to output risk predictions with respect to Fuchs' dystrophy may include categories or values representing a patient's risk or likelihood of corneal decompensation after cataract surgery. In yet another example, the AI model configured to output risk predictions with respect to graft rejection may include categories or values representing a patient's risk or likelihood of a reversal response through steroid treatment.

As an example, the AI model 160 may be trained to predict a risk of progression for one or more particular conditions of the cornea or anterior segment of the eye. In operation, the input layer receives the data input, which is then processed through the convolutional and pooling layers before the processing is passed to the fully connected layers. After being processed through the fully connected layers, the nodes of the output layer receive the output activation values generated by the nodes of the last fully connected layer. The output nodes then process the activation values to generate a model output comprising a risk prediction.

In some embodiments, with respect to FIG. 5, the AI model 160 may additionally or alternatively be configured for generating an action prediction, such as a prediction of an action to be taken with respect to the patient's cornea or anterior segment. The AI model 160 is configured to output a discrete value or category corresponding to the predicted action. In one example, the AI model 160 is configured to output a prediction with respect to dry eye and includes categories or values representing a patient's likelihood of responding to just use of artificial tears, use of steroids, or use of autologous serum tears. The AI model 160 may also present the treatment option that would work best according to the historical data it was trained on. In another example, the AI model 160 is configured to output a prediction with respect to keratoconus eyes that includes categories or values representing a patient's likelihood of responding or requiring cross linking treatment (e.g., because the condition is progressing, while others may have a stationary condition and only need to be observed). Some may have scarring and need keratoplasty. Some patients may improve with contact lenses while others will not. The AI model 160 may therefore output the best course of action.

As an example, the AI model 160 may be trained to predict an action to be taken with respect to the patient's cornea or anterior segment that relates to one or more particular conditions of the cornea or anterior segment of the eye. In operation, the input layer receives the data input, which is then processed through the convolutional and pooling layers before the processing is passed to the fully connected layers. After being processed through the fully connected layers, the nodes of the output layer receive the output activation values generated by the nodes of the last fully connected layer. The output nodes then process the activation values to generate a model output comprising an action prediction.

In some embodiments, with respect to FIG. 5, the AI model 160 may additionally or alternatively be configured for generating a treatment prediction, such as a prediction of treatment to be taken with respect to the patient's cornea or anterior segment. The AI model 160 is configured to output a discrete value or category corresponding to the predicted treatment. As an example, the AI model 160 may be trained to predict a treatment to be taken with respect to the patient's cornea or anterior segment that relates to one or more particular conditions of the cornea or anterior segment of the eye. In operation, the input layer receives the data input, which is then processed through the convolutional and pooling layers before the processing is passed to the fully connected layers. After being processed through the fully connected layers, the nodes of the output layer receive the output activation values generated by the nodes of the last fully connected layer. The output nodes then process the activation values to generate a model output comprising a treatment prediction.

In some embodiments, condition prediction subsystem 112 may generate health analysis data based on one or more predictions (e.g., obtained via one or more prediction models) or other information. In some embodiments, the predictions and other information may be stored in one or more databases (e.g., a historical database, a training database, etc.). As an example, one or more predictions generated with respect to a subject (e.g., based on current images of the subject's eyes) and historical information (e.g., prior predictions generated based on prior images of the subject's eyes or other historical information) may be used to generate the health analysis data, a health report that includes the health analysis data, or other items. In one use case, the historical information may be used to identify an improved or worsening condition, demonstrate comparisons, or provide other information in the health report. In another use case, where the predictions include a set of condition scores (e.g., severity scores, probability scores, or other scores), the health analysis data may be generated based on the condition scores. Using the health analysis data and the predicted likelihood of one or more medical conditions, condition prediction subsystem 112 may generate (i) a predicted level of severity as a condition level, (ii) a predicted severity score for one or more medical conditions (e.g., those having a predicted likelihood above a predetermined threshold), (iii) a predicted risk for one or more medical conditions, (iv) a predicted action for one or more medical conditions, (v) a predicted treatment for one or more medical conditions, or (vi) other predictions. As an example, the probability scores may be utilized to correlate (i) a severity score (e.g., increasing a severity score corresponding to a probability of the condition above a threshold probability), (ii) a discrete risk value or category (e.g., increasing a risk category corresponding to a probability of the condition above a threshold probability), (iii) a discrete value or category for an action, (iv) a discrete value or category for a treatment, or (v) other information. In a further example, probability scores may be analyzed to apply a weighted algorithm to determine a severity level, a severity score, a predicted risk, a predicted action, a predicted treatment, or other information.

It will be appreciated that multiple predictions may be made utilizing one or more networks. Multiple sets of scores may be generated. The sets of scores may be specific to particular conditions. A single model may generate multiple sets of scores. As noted elsewhere, scores and predictions may be generated by an ensemble of networks. The networks may be integrated (e.g., sharing input or output data or having combined combinations of network layers). It will also be appreciated that the system 100 may include an AI model 160 comprising multiple AI networks or models (e.g., submodels) as described above and elsewhere herein. For example, the AI model 160 may include a submodel for generating a condition prediction and one or more submodels for generating ancillary predictions corresponding to the condition prediction (e.g., severity, risk, action, treatment, progression, etc.). In various embodiments, the AI model 160 may comprise a network architecture as described herein with respect to FIGS. 14-18 or elsewhere herein. In various embodiments, the AI model 160 includes multiple submodels. In various embodiments, any of the above AI models 160 may include (e.g., integrate or operatively combine with) the AI model 160 described with respect to FIGS. 12-13. Similarly, any of the above AI models 160 may incorporate patient data, such as demographics data, as described with respect to FIG. 11A-11C.

Figure 11A:
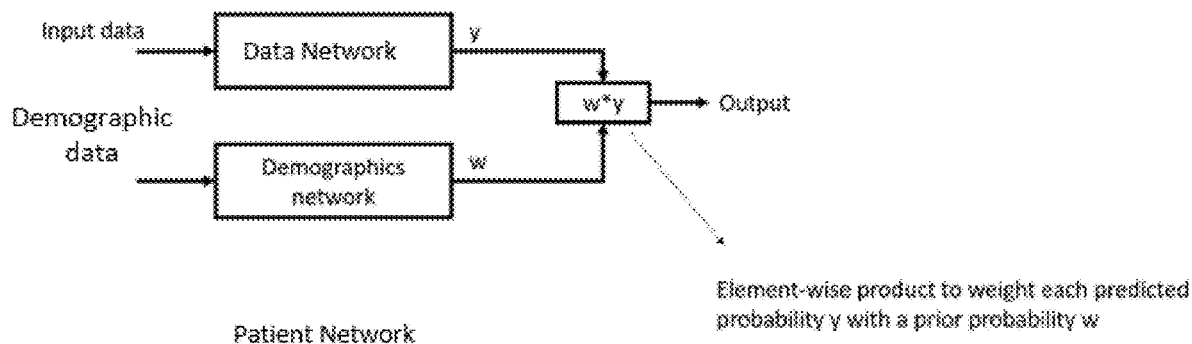
FIGS. 11A-11C illustrate schematic diagrams that include augmentation of an AI model with patient data, in accordance with one or more embodiments.
Figure 11B:
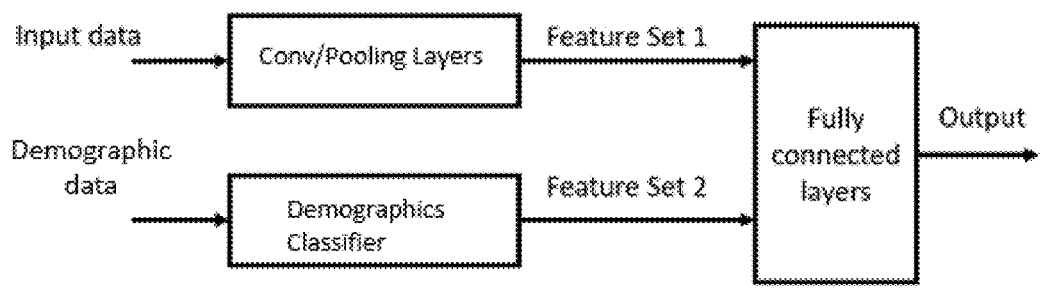
Figure 11C:
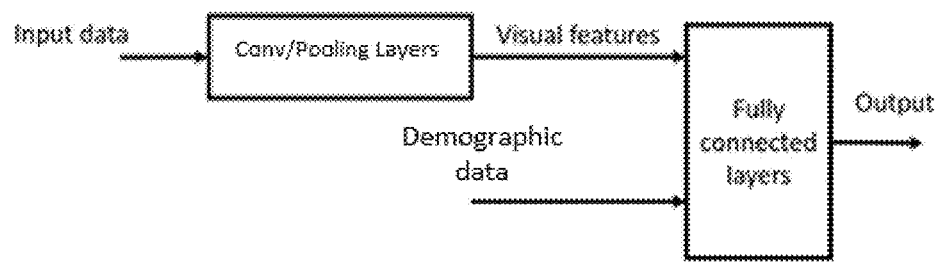

FIGS. 11A-11C schematically illustrates augmentation of the AI model 160 with patient data, in accordance with one or more embodiments. The patient data may include demographics data, medical data, or other patient data. As an example, the AI model 160 may be trained and tuned to process input data to generate a desired output prediction, such as a category likelihood, a disease prediction, a severity prediction, a severity score, a risk prediction, an action prediction, a treatment prediction, or other prediction. The input data may include B-scans, color images, thickness maps, heat maps, bullseye maps, structure maps, or other input data.

With respect to FIG. 11A, in various embodiments, patient data may be incorporated via a demographics network. The demographics network may comprise an AI model 160 such as a Bayesian Model. In another embodiment, the demographics network includes a part of an AI model 160 comprising a neural network trained on patient data. In one example, such a neural network may be trained on patient data only. In some embodiments, the demographics network may be implemented as a shallow neural network consisting of fully connected layers only. In one embodiment, the demographics network comprises an AI model 160 or submodel thereof utilizing classical machine learning, such as Support Vector Machines (SVM) or Discriminant Analysis. As shown in FIG. 11A, the demographics network is configured to receive input data comprising patient data or demographics data and to generate output weights w with respect to one, more, or all y outputs. The final output, which may be generated by a combined output layer for both networks or by an analysis subsystem, as described herein, may be determined by calculating an element-wise product to weight each prediction value y with a prediction value w determined from the patient network taking as input data the patient related data. In the illustrated embodiment, the output y comprises a predicted probability based on image data, thickness maps, heat maps, structure maps, and/or bullseye maps, and the output w from the patient network comprises a prior probability.

With respect to FIG. 11B, the AI model 160 may incorporate patient data comprising demographics data using a demographics classifier output as additional features to the fully connected layers of the CNN or extension thereof. FIG. 11B illustrates an example, of a converging network that shares a fully connected layer block. The demographics classifier is configured to receive input data comprising demographics data, process the input data, and output feature set 2, which may be a set of activation values generated by the processing of demographics input data. Feature set 1 is output by the CNN or a portion thereof. For example, a base block of a CNN including convolutional and pooling layers, which in some embodiments may be a pre-trained network with tuning comprising a plurality of convolutional and pooling layers. In some embodiments, the pre-trained network with tuning also includes one or more fully connected layers and, in one embodiment, an output layer, positioned before the network converges with the patient network at the shared fully connected layers. An output layer (not shown) may be stacked on the last shared fully connected layer to provide an output prediction that includes the processing of both sets of input data through the network. In one embodiment, the output layer stacked on the last shared fully connected layer may include a classification layer as described herein.

With respect to FIG. 11C, the AI model 160 may incorporate patient data comprising demographics data by directly feeding the patient data as features to the fully connected layers of the CNN or extension thereof. The AI model 160 provides an example of an AI model 160 that shares a fully connected layer block by receiving input from multiple sources. The output of the convolutional and pooling layer block includes activation values corresponding to visual features identified in the input data. These visual features may be output from convoluted or pooling layers.

In various embodiments, the integrated networks of FIG. 11A and/or FIG. 11B may be trained jointly. For example, training may include defining global loss function based on the output of individual networks and tuning all the networks accordingly.

In various embodiments, the AI model 160 may include spatial weighting to further improve accuracy. For example, training the network may include identification of areas of interest in input data. Such areas are identified as having the highest probability to allow the AI model 160 to categorize the input data (e.g., images via their activation maps). Using this knowledge, the AI model 160 may be remodeled to look specifically at those areas of interest that have improved accuracy of the algorithm and give those areas more weight. In some embodiments, the AI model 160 may be built off a pre-trained network (e.g., convolutional/pooling layer block) trained with non-medical images and subsequently tuned with medical images such as B-scans, thickness maps, heat maps, structure maps, or bullseye maps. In other embodiments, the AI model 160 may be built off a pre-trained network (e.g., convolutional/pooling layer block) trained with medical images. The AI model 160 may be further tuned with B-scans, thickness maps, heat maps, structure maps, or bullseye maps.

Figure 12:
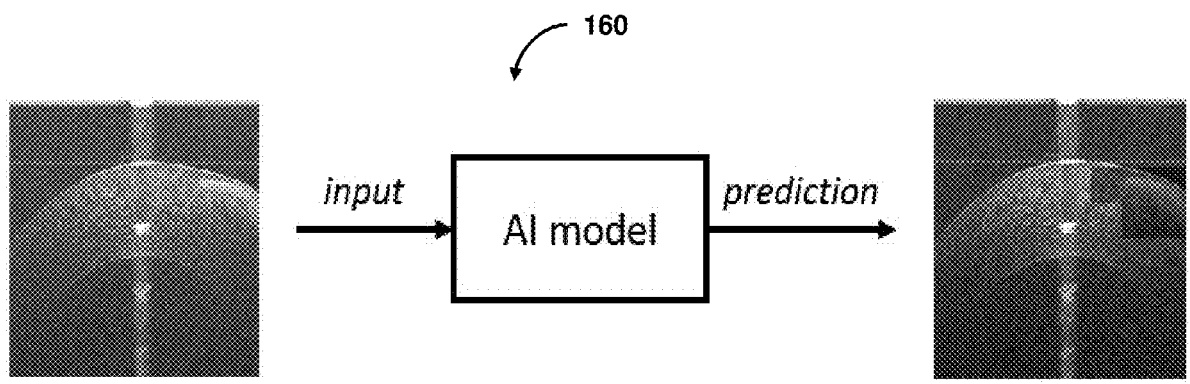
FIG. 12 illustrates a schematic diagram that includes an AI model configured to identifying regions important to predictions of certain conditions of the cornea or anterior segment of the eye, in accordance with one or more embodiments.

FIG. 12 illustrates the AI model 160 configured to identify important regions of input data, in accordance with one or more embodiments. The identification of the important regions in the output may be used to increase the relative weight given to those regions in the algorithm executed by the CNN or other neural network for making diagnosis, risk, treatment, action, or severity predictions with respect to a corneal or anterior segment condition. While shown as being part of system 100, in one embodiment, the AI model 160 for identifying important regions of input data may be a separate AI model, which may not be part of system 100. In another embodiment, the AI model for identifying important regions of input data comprises a neural network, which may be an AI submodel of AI model 160 or the same neural network as the neural network for making diagnosis, risk, treatment, action, or severity predictions with respect to a corneal or anterior segment condition (or a version of such neural network). Accordingly, the AI model 160 may include a separate or same model for important region identification. In one example, a same model may be used using an occlusion test. In another example, a different model may be used with respect to modifying the trained network to output an image instead of scores for the conditions.

As illustrated in FIG. 12, a B-scan image is taken as an input, and the AI model 160 highlights the regions that are important to predict certain conditions in the input image as an output. In some embodiments, the AI model 160 of FIG. 12 may also be configured to predict one or more of disease, severity, risk, treatment, action, layer segmentation, or combination thereof. The AI model 160 may include integrated or separate submodels (e.g., joint, combined, or stacked). The regions may be detected in the input image from which a prediction is to be generated. The AI model 160 may have B-scan images or thickness maps as input, for example, with a target to highlight important features in the input image. Therefore, the input in these configurations will typically be an image such as a thickness map or B-scan. However, in one embodiment, an image such as a heat map may be used as input. In some embodiments, B-scans, thickness maps, and/or heat maps may be used. Other patient data may also be used to give prior probability to the image regions. For example, patient data such as demographics or conditions associated with the patient's other eye may be input to the AI model 160 as described in more detail elsewhere herein and incorporated into the output (e.g., as weighting).

Figure 13:
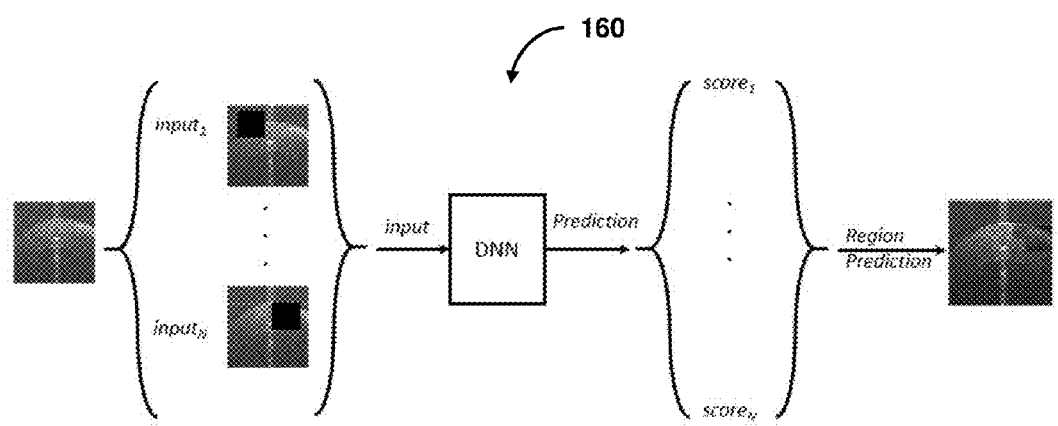
FIG. 13 illustrates a schematic diagram in which an occlusion test is performed to identify the important regions in the input image, in accordance with one or more embodiments.

FIG. 13 illustrates an embodiment of the system 100 according to FIG. 12. In this embodiment, the AI model 160 includes a DNN and an occlusion test is used to find the important regions in the input image. Multiple copies of an image are input into the AI model with different portions of the image occluded. By comparing the output prediction scores of the various occluded images to an output prediction score obtained from the image without occlusion, important regions may be identified. That is, the occluded parts of the image that account for the largest drop in the prediction likelihood may be deemed to be associated with the most important parts in the input image. In some embodiments, the AI model 160 may be configured to output an image that highlights these regions. In the illustrated embodiment, the regions are highlighted in green in the output of the AI model 160. Thus, the AI model 160 used to predict corneal condition probabilities or a similar AI model may be used to predict important regions in the input image where the parts of the image with lower output scores are chosen as the most important, which may be the case when only using the occlusion test. In some embodiments, the system 100 may include the AI model for predicting important regions for incorporation of the identification of important regions into the AI model 160. In the illustrated embodiment, the system 100 outputs the important regions in a report, which may be further incorporated into a health report by an analysis subsystem, but does not receive the important regions as an input. In other embodiments, the system 100 may receive such information as input or for incorporation into the AI model 160. In one embodiment, system 100 includes a preprocessing subsystem that includes the AI model for identification of important regions. In one example, the AI model 160 may be implemented to identify important regions during training and such data may thereafter incorporated into the AI model 160 to improve prediction accuracy.

In some embodiments, B-scan images may be preprocessed before identification of important regions. The identification of these regions may be done after the prediction in training data. The predicted regions may be considered part of the generated report and may not be used to enhance a prediction with respect to the image in which the identification relates. However, the predicted regions may be used to further improve prediction to train the networks by guiding the algorithm to look at specific regions to give them more weight.

In another embodiment, where the AI model 160 is configured to identify important regions, the data obtained from the identification of the important regions may be used to modify the last layers of the convolutional/pooling layer portion of a trained network. For example, the modification may comprise grouping the final activation maps of this portion of the network using weights between them and the first fully connected layer. This combination may be used to generate a probability map of the important regions in the images based on the trained network, which may translate to fixed regions for all images and which is different than the occlusion test method.

In addition to improving future predictions by incorporating important region findings in subsequent iterations of the AI model 160, eye professionals may examine images or eyes a look to specific areas for diagnosis of conditions of the cornea or anterior segment. The AI model, however, may train the algorithm to look at regions previously unknown to correlate with a condition. Thus, the report generated identifying important regions to the diagnosis provides information regarding how the AI model is operating and provides insight into additional locations where conditions of the cornea and anterior segment may impact or that may be used to provide a basis for diagnosis or other prediction, such as severity, risk, progression, prognosis, treatments, etc., related to those conditions.

In some embodiments, the AI model 160 may implement supervised deep learning methods, with labeled input data, be used to improve the corneal layer segmentation task. For example, supervised deep learning methods, with labeled input data, may be used to divide the image into foreground (the cornea) and background. The epithelium and endothelium may be defined as top and bottom boundaries of the cornea. In another embodiment, unsupervised deep learning methods may also be used for the segmentation of the anterior segment and epithelium and endothelium, thereby overcoming the problem of labeling the data which requires a lot of time from experts and specialized trained operators. This approach also has the advantage that it can be done using supervised learning with labeled images and used with unsupervised learning by using clustering without any labeling.

In some embodiments, the preprocessing subsystem 114 may further process the image data to denoise the input image or may generate thickness maps, heat maps, structure maps, or bullseye maps. In one example, the preprocessing subsystem 114 produces images of one or more layers from the segmented image data for input into the AI model 160. For example, the preprocessing subsystem 114 may remove one or more segmented layers from the image data. In some embodiments, preprocessing subsystem 114 may segment one or more images and transmit the segmented image data or data derived therefrom to one or more other subsystems.

Figure 14:
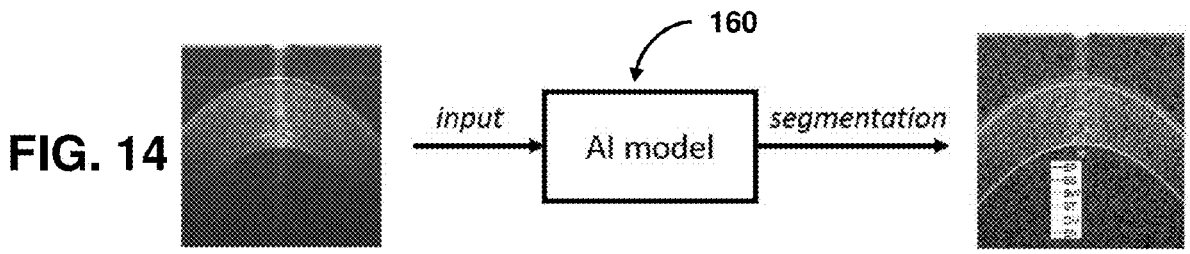
FIG. 14 illustrates a schematic diagram that includes an AI model for segmenting corneal layer boundaries, in accordance with one or more embodiments.

FIG. 14 illustrates a segmentation operation performed by the AI model 160 to segment the corneal layer boundaries, in accordance with one or more embodiments. The AI model 160 takes the OCT B-scan as an input and produces the segmentation of the layer boundaries as the output of the AI model 160. The AI model 160 may divide the image into foreground (the cornea) and background. The epithelium (EP, purple) and the endothelium (EN, orange) may be defined as top and bottom boundaries of the cornea. This technique may then be extended to the segmentation to other microlayers of the cornea by sequential identification of subsequent top and bottom boundaries, namely, basal-epithelial (BS, light blue), bowman's (BW, aqua), stroma (ST, green) and descemet's (DM, yellow). For example, the AI model 160 may work from the anterior and/or posterior inward to identify segmentation boundaries. In various embodiments, the AI model 160 comprises a semantic network, such as Region-based Convolutional Neural Network (R-CNN), Fully Convolutional Networks (FCN), U-Net, or SegNet for the segmentation of the anterior segment and for the segmentation of the epithelium and the endothelium of the cornea. The AI model 160 takes OCT B-scan images as input and generates the segmentation layer boundaries as the output of the model.

Figure 15:
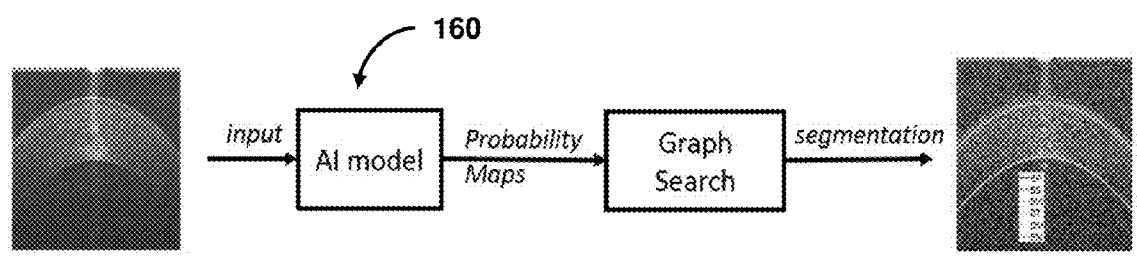
FIG. 15 illustrates a schematic diagram that includes an AI model for segmenting corneal layer boundaries, in accordance with one or more embodiments.

FIG. 15 illustrates another embodiment in which the AI model 160 is configured to segment the corneal layer boundaries. The output of the AI model 160 may include a probability map for each boundary. These maps can be further processed using graph search to find the final segmentation.

Figure 16:
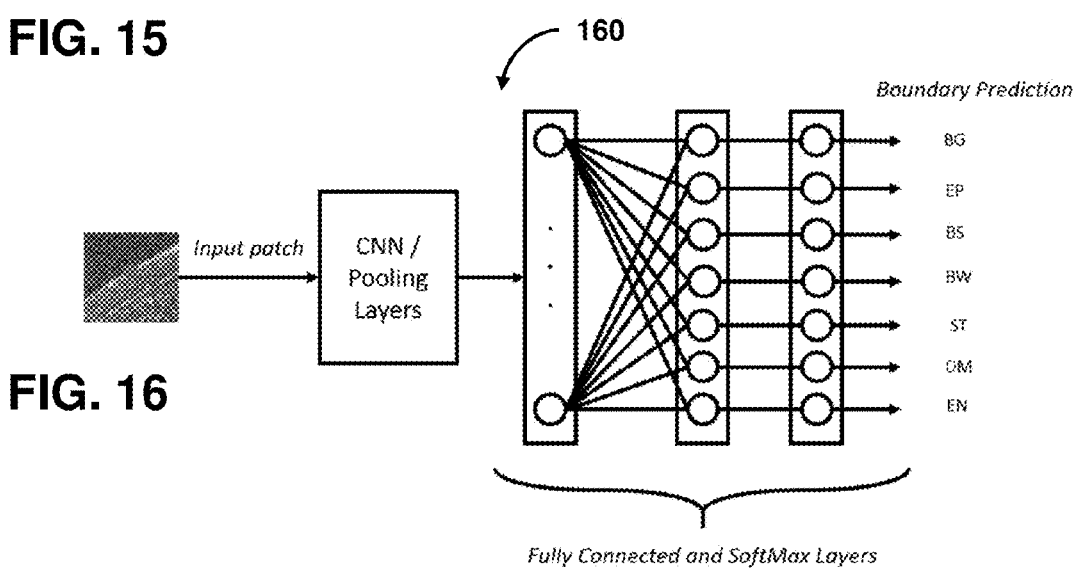
FIG. 16 illustrates a schematic diagram that includes an AI model for generating boundary predictions for corneal layer segmentation, in accordance with one or more embodiments.

In some embodiments, with respect to FIG. 16, the AI model 160 may take as input a small patch of a high definition image (e.g., OCT B-scan) and predict whether the patch belongs to the background (BG) or one of the boundaries: (EP)—epithelium, (BS)—basal epithelium, (BW)—bowman's layer, (DM)—descemet's membrane, (EN)—endothelium, as shown in the architecture of FIG. 16. As an example, the AI model 160 outputs the probability of the input patch that represents the likelihood of the center of the patch belonging to the background and each of the boundaries. By repeating this for all pixels, a probability map of all pixels belonging to each category may be constructed.

Figure 17:
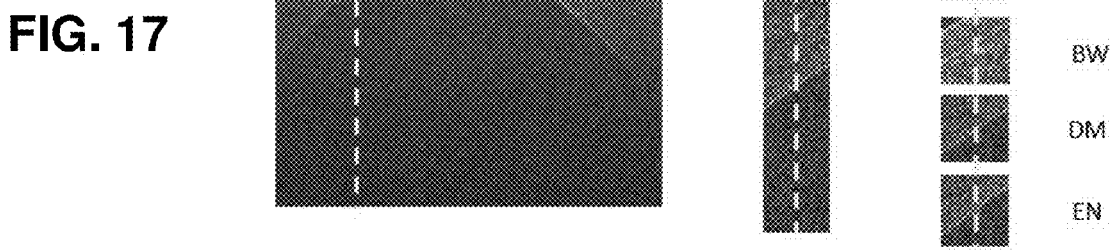
FIG. 17 illustrates a schematic diagram of a patch extraction technique for generating a training dataset and training an AI model, in accordance with one or more embodiments.

FIG. 17 illustrates patch extraction from a B-scan image for generating a training dataset and training an AI model, in accordance with one or more embodiments. The B-scan is shown in panel I. At each A-scan, indicated by the broken vertical line, 7 patches are extracted, one patch belonging to the background (BG) and 6 patches where each one of them belongs to each boundary. As shown in panel II, lateral regions flanking the A-scan are also included in the patches shown in panel III. The A-scan is generally centrally positioned in the patch, but in other embodiments the A-scan may be positioned to the left or right of center. This extraction procedure may be repeated for additional A-scans, or all A-scans, making up the B-scan. The extracted patches from the image may be added to extracted patches from the other images to construct a training dataset for the AI model 160.

Testing may be performed similarly where the input image is divided into patches. The patches may be classified by the trained network to give the probability maps of the input image pixels. These probability maps may then be used with graph search to segment the boundaries (e.g., the probabilities of the pixels in the probability maps may be used to identify paths of minimum weight for interface boundaries). Threshold values may be used in one example. Various graph search techniques may be used. In some embodiments, the graph search may be weighted or unweighted.

With further reference to FIGS. 18-23, in various embodiments, the AI model 160 output condition scores that relate to a set of conditions. The set of conditions scores may further include one or more corresponding scores that additionally relate to ancillary aspect predictions corresponding to the condition such as severity, risk, action/treatment, progression, prognosis, or other predictions corresponding to one or more of the conditions. In various embodiments, the system 100 may include an AI model 160 comprising a plurality of submodels for each predicted condition configured to predict severity, risk, treatment, progression, prognosis, or other ancillary aspect prediction corresponding to the particular condition. In some embodiments, the AI model 160 may include a combined architecture to perform multiple predictions, such as multiple predictions corresponding to a single condition or multiple predictions corresponding to multiple conditions. For example, a single network may be configured to generate one score including multiple conditions. This approach may include dividing the data based on all the conditions to have specific data for each augmented category. In one example, a score may correspond to a category comprising a prediction of a condition and one or more ancillary aspects corresponding to the condition (e.g., one or more of severity, risk, action, treatment, progression, prognosis, etc.). In another embodiment, a set of condition scores may be generated for multiple conditions and one or more ancillary aspects selected from severities, risks, actions, treatments, or combinations thereof for one or all of the conditions. In some embodiments, after the system 100 generates a prediction of a condition, the input data upon which the prediction is based may be automatically fed to submodels to generate ancillary aspect predictions corresponding to the condition, such as severity, risk, action, treatment, progression, prognosis, etc. In some embodiments, submodels for ancillary aspect predictions may be specific to a condition (e.g., trained for prediction of risk level for dry eyes) or may be generic to one or more conditions.

Figure 18:
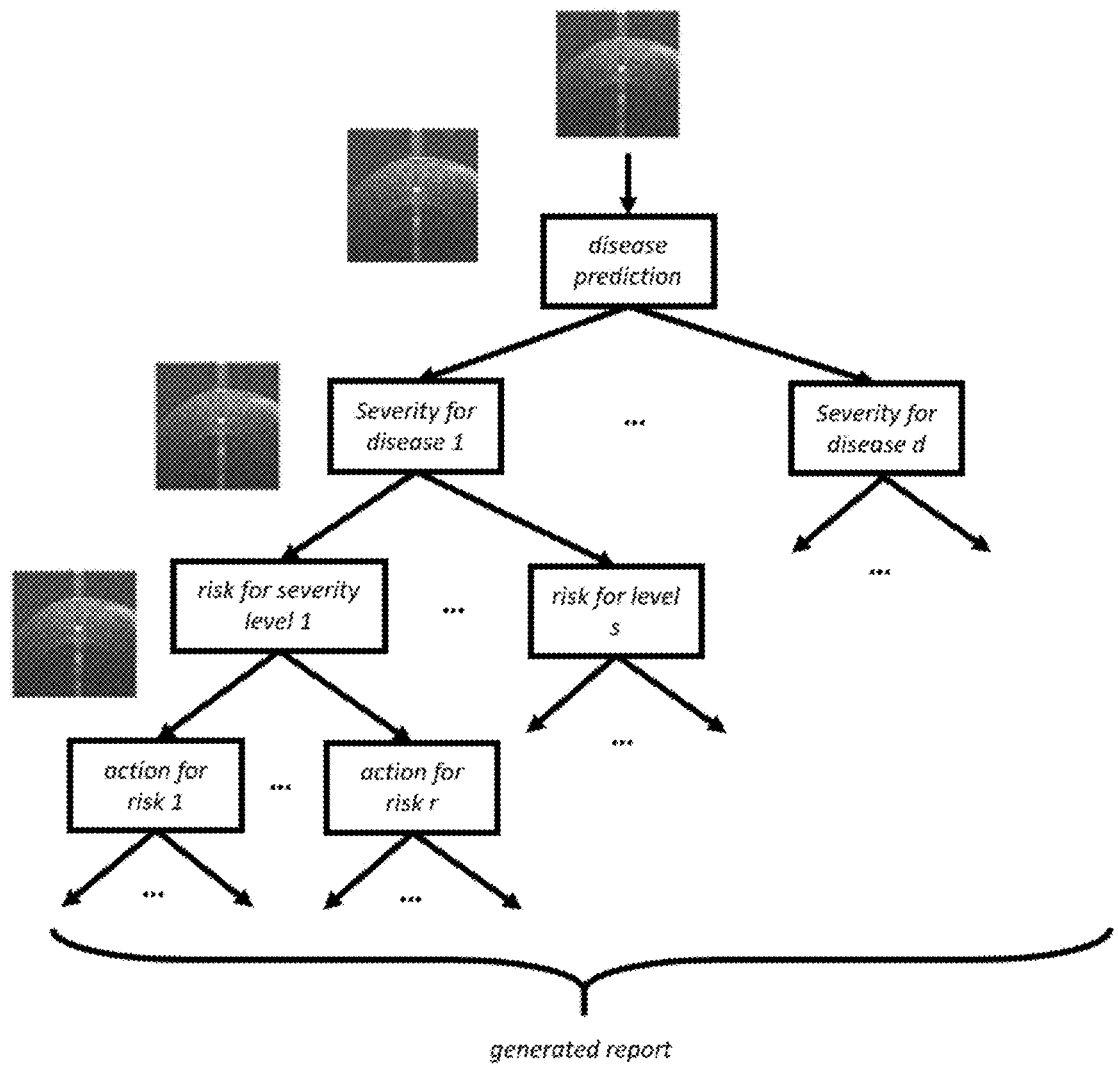
FIG. 18 illustrates a schematic diagram that includes a hierarchical, cascading architecture, in accordance with one or more embodiments.

FIG. 18 schematically illustrates the AI model 160 configured to include a plurality of submodels arranged in a hierarchical design having a cascade configuration, in accordance with one or more embodiments. As an example, the input data (e.g., a B-scan) is input into a first tier submodel 160a for generating a condition prediction. The condition prediction (e.g., highest or threshold probability) determines which condition-related submodel the input data is to be processed for the next ancillary aspect prediction related to the condition in the following tier. Thus, in this AI model 160, the condition and ancillary aspect predictions in preceding tiers are related. In this example, submodel 160a predicts condition 1. Accordingly, the input data is fed into second tier submodel 160b which is trained to output severity predictions for condition 1. Prediction of another condition category results in the input data being fed into the corresponding second tier submodel for that condition, and these submodels are identified by condition d.

In this embodiment, submodel 160b outputs severity levels, but in other embodiments, severity may be output as a score instead of a discrete value. The severity level predicted from submodel 160b determines the third tier submodel that the input data will be fed. As shown, submodel 160b outputs severity level 1 and the input data is provided as input into submodel 160c, which is trained to output risk predictions for condition 1 and severity level 1. Prediction of another severity level results in the input data being fed into the corresponding third tier submodel for that severity level, and these submodels are identified by risk for levels.

Submodel 160c outputs risk 1, which results in the input data being provided to submodel 160d trained to output action predictions for condition 1, severity level 1, and risk 1. Prediction of another risk results in the input data being fed into the corresponding fourth tier submodel for that risk, and these submodels are identified by action for risk r. The output prediction of submodel 160d may similarly determine subsequent submodels for subsequent ancillary aspect predictions, such as progression or prognosis with or without undertaking the predicted action from submodel 160d. The predictions from each submodel 160a-160d may be provided in a report.

It should be noted, that in some embodiments, one or more of the submodels for ancillary aspect predictions related to the condition may be generic for the condition or for other ancillary aspect conditions. For example, a risk may be generic for two or more severity ranges or levels. In another embodiment, the condition prediction from submodel 160a results in the input data being input into each submodel of a set of condition-related submodels for the condition predicted, the selection of which does not relate to the prediction of a subsequent condition-related submodel. The set of condition-related submodels may include a model for each ancillary aspect prediction to be made (e.g., severity, risk, treatment, action, progression, prognosis, etc.) As noted above, multiple conditions may be predicted (e.g., based on having associated probabilities above a threshold). In some such embodiments, the input data may be input into a different set of condition-related submodels as well. In further embodiments, the input data may be input along a condition-related submodel cascade for additional conditions (e.g., when output probabilities for multiple conditions are above threshold probabilities for each of the conditions of conditions).

FIG. 19A schematically illustrates the AI model 160 being augmented to generate an augmented category, in accordance with one or more embodiments. The AI model 160 may be trained to output scores corresponding to an augmented category that includes a single score corresponding to a condition and one or more ancillary aspect predictions corresponding to the condition. A health report may be generated using one network to generate an augmented category including all the values needed for the report. The AI model 160 may be trained using training data comprising grouped images that are labeled and annotated for a condition and one or more ancillary aspect predictions. The AI model 160 may use all the annotations at the same time for category prediction. For example, the table in FIG. 19B illustrates that a category (Ck) may be based on 5 annotations (dk, sk, rk, ak, tk) wherein the presence of the 5 annotations corresponds to a label of the corresponding category (Ck) being used. Thus, a label or category may be included for each combination of condition, severity, risk, action, and treatment. In some embodiments, different, fewer, or more annotations may be grouped in categories. Further to the above, the AI model 160 includes an augmented model to generate an analysis report, which may be a health report. The augmented model is designed as one model that can do all classification tasks at one time. However, in some embodiments, multiple combinations of augmented submodels may be used that perform subsets of classification tasks (e.g., combinations of condition, severity, risk, action, or treatment). The augmented model may be constructed by dividing training data at a detailed level. For example, training data related to a specific condition, specific risk, specific treatment, specific action, and specific treatment may be grouped together and these labels will be encoded into a unique augmented label that represents this combination of the original labels. The augmented label will be used in the training. In this way, multiple models may be combined into one model. Such an augmented model takes as input the data divided at very fine levels along with augmented labels. FIG. 19C illustrates the AI model 160 in FIG. 19A, where the AI model 160 includes a convolutional/pooling layer block, fully connected layers, and a SoftMax layer.

Figure 20:
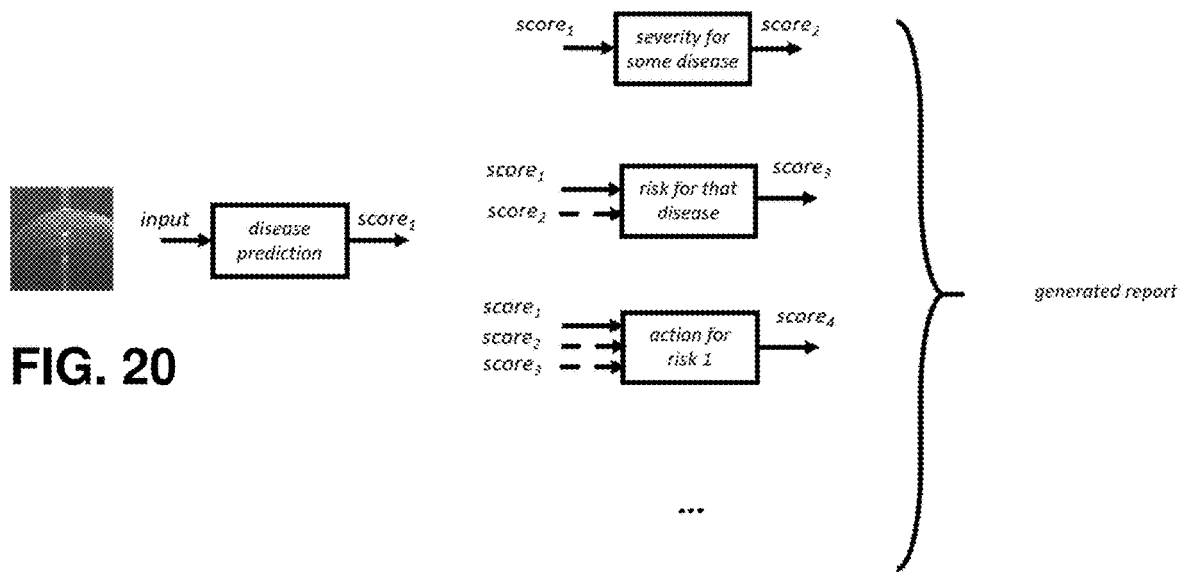
FIG. 20 illustrates a schematic diagram that includes an AI model having hierarchical architecture utilizing prediction scores, in accordance with one or more embodiments.

FIG. 20 schematically illustrates an embodiment of the system 100 wherein the AI model 160 is configured to output a condition prediction and one or more ancillary aspect predictions related to the condition. In this embodiment, the AI model 160 includes a plurality of submodels 160e-160h. The output score of the first submodel 160e may be used to determine ancillary aspect predictions related to that output. For example, submodel 160e outputs a $score_1$. Thus, in some embodiments, the AI model 160 may include a cascade aspect similar to that described with respect to FIG. 18. That $score_1$ may indicate a condition or may be used by a submodel trained to take that output $score_1$ and determine an ancillary aspect prediction, which may be a score that may or may not ultimately be converted to a category label. As shown, $score_1$ is used as input into submodel 160f which outputs a $score_2$ corresponding to a severity for a condition. In some embodiments, submodel 160ƒ is generic for one or more conditions and the severity score of submodel 160ƒ indicates a condition prediction from which it corresponds. In another embodiment, submodel 160ƒ is specific to a condition and is only triggered to fire if $score_1$ is suitable (e.g., positive) or calculates a suitable $score_2$. $Score_1$ is also input into submodel 160g to generate a $score_3$ corresponding to a risk for the condition corresponding to the severity generated by submodel 160ƒ. As indicated by the broken arrow, submodel 160ƒ may, in some embodiments, optionally take as input $score_2$. $Score_1$ is also input into submodel 160h to generate a score4 corresponding to an action for the risk $score_3$ generated by submodel 160g. As indicated by the broken arrows, submodel 160h may, in some embodiments, optionally take as input $score_2$ and/or input $score_3$.

It will be appreciated that the order of ancillary aspect prediction submodels and the particular input score combinations may be arranged differently for some conditions within the AI model 160 or other AI models configured to provide other ancillary aspect predictions.

The scores may be obtained from a SoftMax layer before the scores are converted into category labels. That is, model outputs include scores or probabilities which can be converted into the label corresponding to the category with the maximum value by the SoftMax layer. The label may be generated for the report, for example. In some embodiments, one or more of submodels 160ƒ, 160g, or 160h comprises a classical classifier. For example, the score or probability output from one or more submodels 160e-160h may be used as input into a classical classifier, such as the SVM, to train it to detect the scores for the ancillary aspect predictions.

Figure 21:
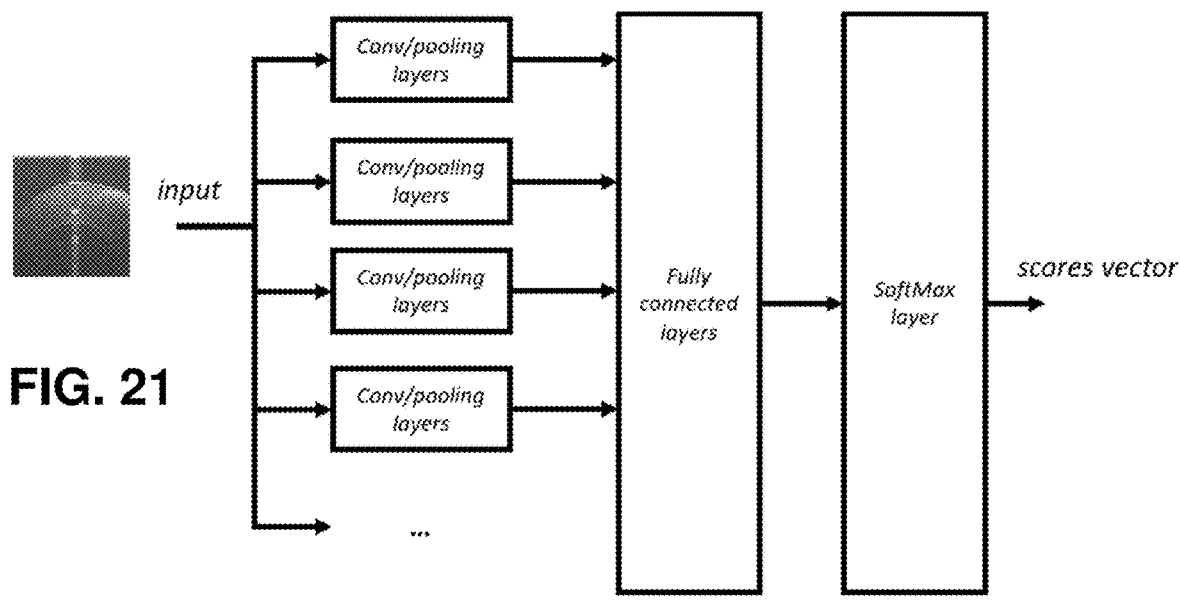
FIG. 21 illustrates a schematic diagram that includes an AI model having multiple specialized convolutional/pooling layer blocks that connect to a same block of fully connected layers, in accordance with one or more embodiments.

FIG. 21 schematically illustrates the AI model 160 being configured to include a joint network that detects all scores at once, in accordance with one or more embodiments. The AI model 160 is an example of a converging network. In contrast to the augmented network described with respect to FIGS. 19A-19C that includes a single convolutional/pooling layers block, this AI model 160 includes convolutional/pooling layer blocks. Each may be trained for a particular condition to allow different features to be extracted for each condition. The last layers of each convolutional/pooling layer block regroup the extracted features into one set of fully connected layers and SoftMax layer.

Figure 22:
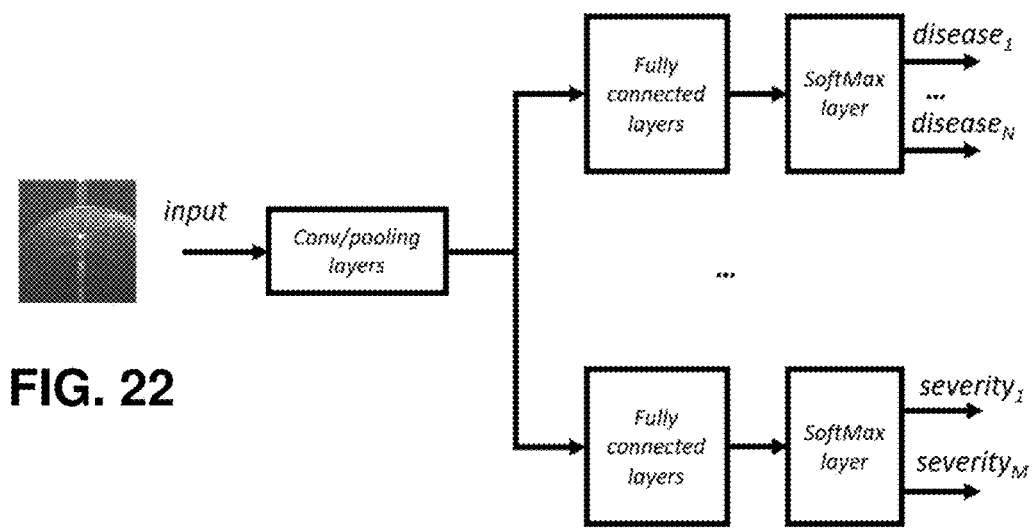
FIG. 22 illustrates a schematic diagram that includes an AI model having a shared convolutional/pooling layer block that feeds multiple specialized fully connected layer blocks, in accordance with one or more embodiments.

FIG. 22 schematically illustrates an embodiment where the AI model 160 includes a combined or combination network using one convolutional/pooling layers block and multiple sets of fully connected layers and SoftMax layers. The AI model is an example of a diverging network. In this case, extracted features will be the same for all conditions. The different predictions share the same set of convolutional and pooling layers, but each has its own fully connected layers and SoftMax layer. As shown, a set of fully connected layers and SoftMax layer may be trained to provide a prediction with respect to a set of conditions. The sets of fully connected layers and SoftMax layer for ancillary aspect predictions may be specific to particular conditions or may be configured to output a type of ancillary aspect prediction for multiple conditions.

An example training process set up in accordance with one or more embodiments may include obtaining labeled data or annotating data to obtain labeled data. The labeled data may include training data such as annotated/labeled images. The method may include dividing the labeled data into subgroups where each has the same label that will be predicted by the network. Each data member of the group will have the same label (or set of annotations) and each label group represents a prediction category that will be predicted by the network. The number of data examples in each group is preferably similar so that the data is balanced to prevent bias in the training process toward a specific label. The training data set may include multiple frames for B-scans. Optionally, all frames for each B-scan can be used. Although the frames represent the same cut, they have different noise patterns and slightly different deformation of the cut. Thus, training with multiple frames may be used to make the network robust to noise. The number of layers and their parameters may be determined on the basis of experiments and cross validation of the training data. Cross validation is done by dividing the training data into a training part and a validation part. The trained network is then used to test the validation part. This process may be repeated by dividing the training data into another different training set and another different validation set which is evaluated with the new trained network. Therefore, the whole training process may be repeated many times with different subsets of the training data and the trained network may be evaluated with different validation subsets. This may be done to ensure the robustness of the trained network. The trained network may then be evaluated using the real testing data.

Figure 23:
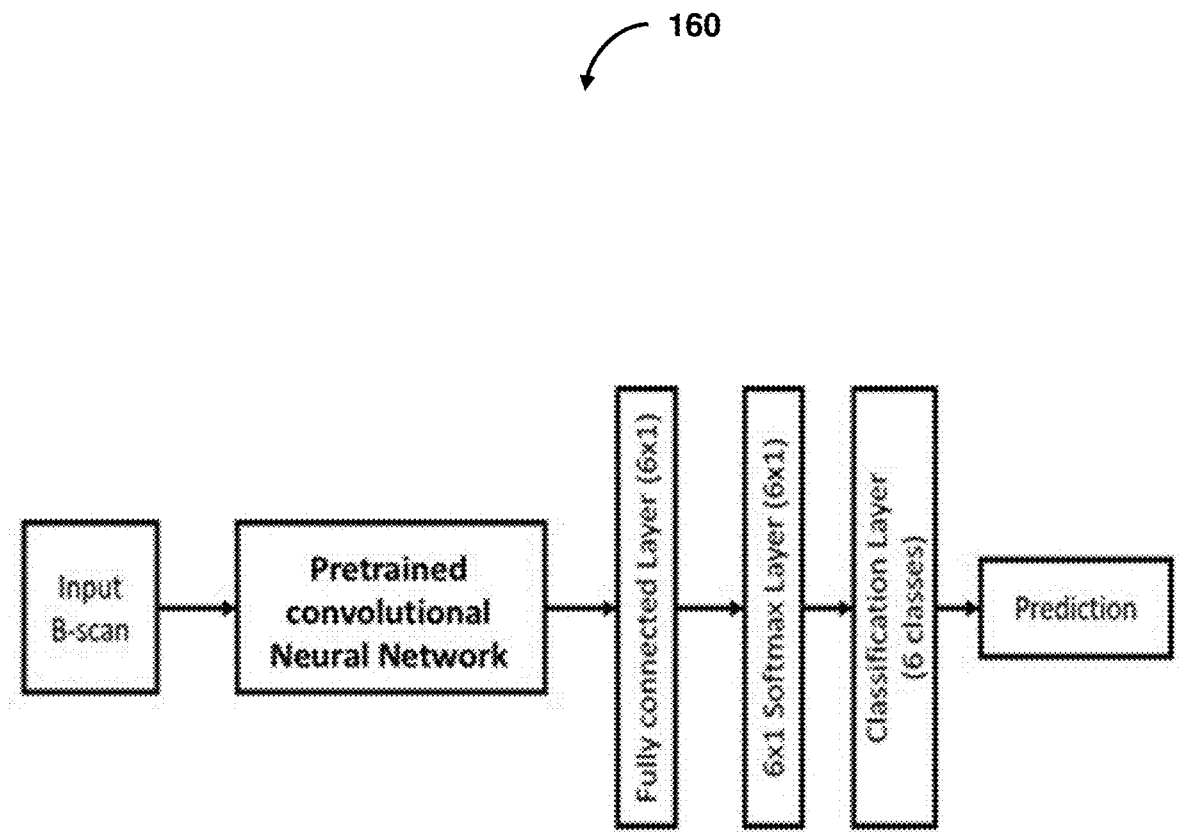
FIG. 23 illustrates a schematic diagram that includes an AI model incorporating transfer learning, in accordance with one or more embodiments.

As an example, with respect to FIG. 23, the AI model 160 includes a set of convolutional and pooling layers followed by a set of fully connected layers and an output layer. In this embodiment, a modified pre-trained network was incorporated into the AI model 160 architecture of the system 100. The initial layers of a convolutional neural network (e.g., convolutional and pooling layers) are important for feature extraction. The extracted features are generic and may be considered data independent. The last layers (e.g., fully connected layers), combine the important features for each class in the data and are typically dependent on the images used. For the AI model 160, these layers were redefined from that of the pre-trained network. In particular, the fully connected layer and output layer were redefined. In this configuration, the output layer used included a SoftMax layer and a classification layer. These layers are modified to be adapted to the new classification task as follows: the fully connected layer is modified to be of a length equal to the number of categories in the prediction task; the SoftMax layer is modified accordingly to convert the output of the fully connected layer into prediction probabilities; and the classification layer was modified to have the labels corresponding to the new classification problem. For example, for the condition prediction task, the length nodes in the fully connected layer were changed to 6 and the labels were changed to {"Control", "Dry eye", "Fuchs Endothelial Dystrophy", "Keratoconus", "Corneal Graft Rejection", "Limbal Stem Cells Deficiency"}. Each label corresponds to a corneal diagnosis.

Microlayer tomography CML-T B-scan data was used to train the parameters of the fully connected layer and tune the parameters of the original network such that the prediction of the network was optimized for the task of corneal diagnosis. For the task of classifying the severity of corneal the conditions the AI model was trained on OCT CML-T images of different condition severity as graded by the cornea specialist.

During the training stage, all available CML-T frames were used without registration or averaging. This helped the AI model 160 become robust to noise because noise is random while corneal microlayers patterns and features are not. The distinct artifacts associated with anterior segment OCT images may or may not exist in another OCT image e.g. specular reflections, and horizontal artifacts. In further embodiments, the accuracy of the AI model may be further improved by using preprocessed OCT images, and removing those artifacts beforehand (e.g., FIGS. 3A-3B and accompanying discussion). In some embodiments, training the AI model 160 comprises training with B-scan images with averaging and/or registration.

To further improve accuracy, after the first training session of the AI model 160, areas of interest on the CML-T OCT images were identified (e.g., FIGS. 12-13 and accompanying discussion). These areas were found to have the highest probability to allow the neural network to categorize the images (activation maps). Using this knowledge, the AI model was further remodeled to look specifically at those areas of interest and give those areas more weight.

In this demonstration, transfer learning with pre-trained networks was used to reduce training time. However, in other embodiments, the feature extraction layers, such as convolutional layers, of the AI model may be trained on medical images. Although, the training data of the network is not medical images, this data helps the network to learn how to extract complex visual features from the image. Convolutional neural networks (such as AlexNet, VGG16, VGG19, and GoogLeNet) may be modified for the classification of corneal conditions using OCT corneal microlayer tomography B-scans (CML-T), thickness maps, and heat maps of the cornea. Here, the last three layers in each network were modified to be suitable for the classification task and then tuned their parameters using approximately 14,000 corneal B-scan CML-T images. These CML-T B-scans represented different corneal conditions and were used as a dataset to train and tune the neural network of the deep learning algorithm. The diagnosis of each of the CML-T B-scan was made by a cornea specialist. Eighty percent of this dataset was utilized for training and 20% was utilized for testing and evaluation of the network.

In this demonstration, the AI model was allowed to provide up to two diagnoses for the same eye (if a second diagnosis was present). The probability of diagnosis was calculated by the network, and if a second diagnosis was calculated to have a probability above a threshold, then that second diagnosis was also provided. For example, the diagnosis could be Keratoconus with Dry eye. The accuracy of the model was further improved by calculating the probability of the diagnosis for each single CML-T OCT B-scan and then getting a mean of probability from the total B-scans of the same eye. The results of the demonstration are summarized in Table. 1.

As can be seen in Table 1, the AI model to classify corneal CML-T B-scans achieved accuracy of 98.85% for the classification task.

TABLE 1

| Label | Training accuracy (%) | Testing accuracy (%) |
| --- | --- | --- |
| control | 97.44 | 96.72 |
| dry | 98.18 | 96.88 |
| fuchs | 99.96 | 99.85 |
| graft_rejection | 99.00 | 98.80 |
| ken | 98.61 | 96.91 |
| stem_cells | 99.87 | 100.00 |
| Overall accuracy | 98.77 | 98.18 |

Figure 24:
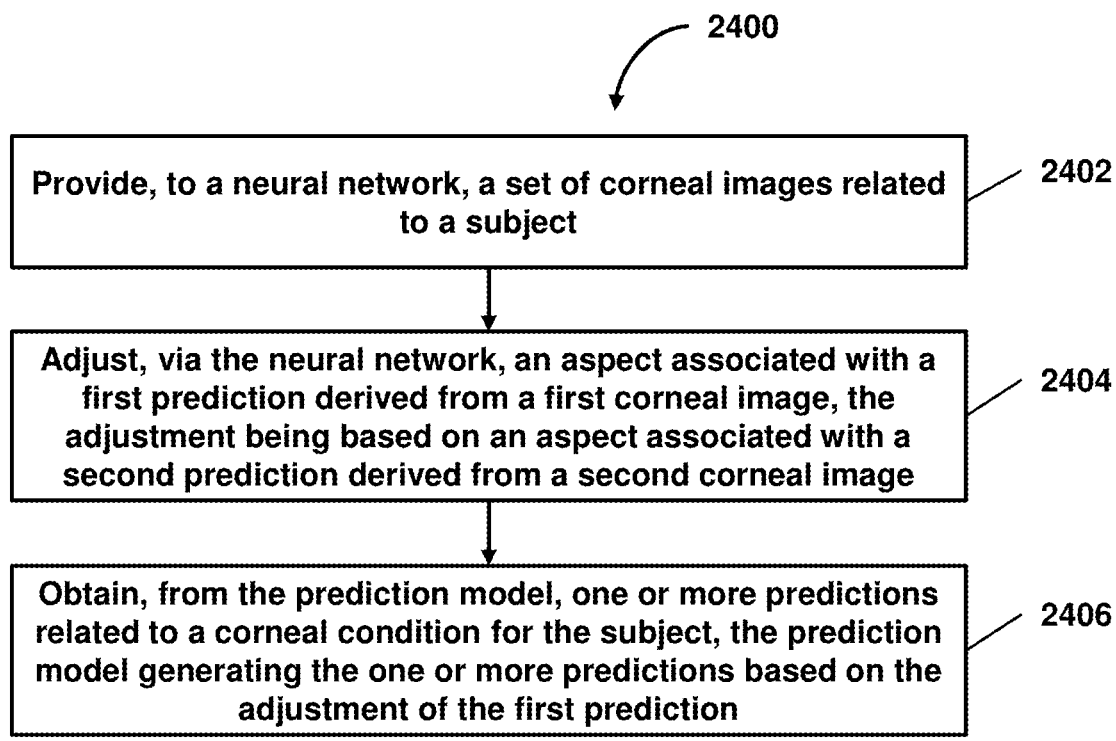
FIG. 24 illustrates a flowchart of a method of facilitating determinations related to eye conditions or treatments thereof, in accordance with one or more embodiments.
Figure 25:
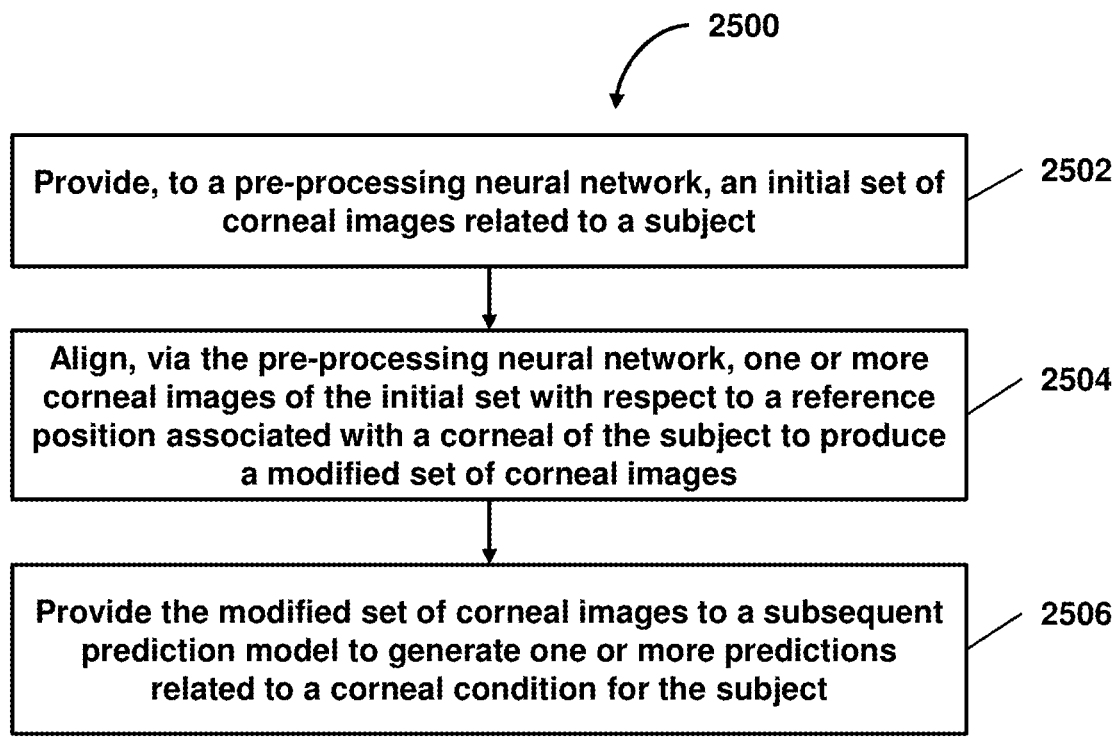
FIG. 25 illustrates a flowchart of a method of facilitating neural-network-based preprocessing of images for a subsequent neural network, in accordance with one or more embodiments.

FIGS. 24-25 are example flowcharts of processing operations of methods that enable the various features and functionality of the system as described in detail above. The processing operations of each method presented below are intended to be illustrative and non-limiting. In some embodiments, for example, the methods may be accomplished with one or more additional operations not described, and/or without one or more of the operations discussed. Additionally, the order in which the processing operations of the methods are illustrated (and described below) is not intended to be limiting.

In some embodiments, the methods may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on an electronic storage medium. The processing devices may include one or more devices configured through hardware, firmware, and/or software to be specifically designed for execution of one or more of the operations of the methods.

FIG. 24 shows a flowchart of a method 2400 of facilitating determinations related to eye conditions or treatments thereof, in accordance with one or more embodiments. In an operation 2402, a set of corneal images related to a subject may be provided to a neural network. As an example, the neural network may include a plurality of layers, such as one or more input layers, hidden layers, and output layers. In one use case, at least one input layer of the neural network may be configured to take corneal images as input to the neural network. At least one hidden layer of the neural network may be configured to obtain multiple predictions related to a corneal condition and adjust an aspect associated with one of the predictions based on an aspect associated with one or more other ones of the predictions. In a further use case, each prediction of the multiple predictions (obtained by the hidden layer) may be derived from a different corneal image of the input corneal images. Operation 2402 may be performed by a subsystem that is the same as or similar to condition prediction subsystem 112, in accordance with one or more embodiments.

In an operation 2404, an aspect associated with a first prediction (derived from a first corneal image of the set) may be adjusted via the neural network. As an example, the adjustment may be performed based on an aspect associated with the second prediction (derived from a second corneal image of the set). Aspects associated with a prediction may include the predicted information, a weight or probability associated with the prediction, a probability associated with the prediction, a portion of an eye (to which the prediction corresponds) or other eye location associated with the prediction, or other aspects. The predicted information may include (i) whether any eye condition is present in the subject or will likely be present in the subject in the future (e.g., currently present in an eye of the subject, the respective risks of such conditions developing in the eye of the subject if corrective treatment or action is taken or not taken, etc.), (ii) severities of such conditions predicted to be present in the subject or severity score associated therewith, (iii) treatments or actions to be taken with respect to such conditions, (iv) probabilities that the eye of the subject will respond favorably or unfavorably to such treatments or actions, or (v) other information. Operation 2404 may be performed by a subsystem that is the same as or similar to condition prediction subsystem 112, in accordance with one or more embodiments.

In an operation 2406, one or more predictions related to a corneal condition for the subject may be obtained from the prediction model. As an example, the prediction model may generate the one or more predictions based on the adjustment of the first prediction. As another example, the predictions may include one or more predictions related to at least one of corneal ectasia, Keratoconus, corneal graft rejection episode and failure, dry eye syndrome (DES), Fuchs' dystrophy, corneal limbal stem cell deficiency, cataract, glaucoma, or other corneal condition. Operation 2406 may be performed by a subsystem that is the same as or similar to condition prediction subsystem 112, in accordance with one or more embodiments.

FIG. 25 shows a flowchart of a method 2500 of facilitating neural-network-based preprocessing of images for a subsequent neural network, in accordance with one or more embodiments. In an operation 2502, an initial set of corneal images related to a subject may be provided to a preprocessing neural network. As an example, the preprocessing prediction model may remove problematic or low-quality images from the initial set of images. As another example, the preprocessing prediction model may perform modifications of one or more images of the initial set of images, such as denoising an image, removing artifacts from an image, aligning an image, or performing other modifications (e.g., to increase the accuracy of a subsequent prediction model's predictions). Operation 2502 may be performed by a subsystem that is the same as or similar to preprocessing subsystem 114, in accordance with one or more embodiments.

In an operation 2504, one or more corneal images of the initial set may be aligned via the preprocessing neural network to produce a modified set of corneal images. As an example, the corneal images may be aligned with respect to a reference position associated with the cornea of the subject, such as a center of the cornea of the subject or other reference position associated with the cornea of the subject. Operation 2504 may be performed by a subsystem that is the same as or similar to preprocessing subsystem 114, in accordance with one or more embodiments.

In an operation 2506, the modified set of corneal images may be provided to a subsequent prediction model to generate one or more predictions related to a corneal condition for the subject. As an example, the predictions may include one or more predictions related to at least one of corneal ectasia, Keratoconus, corneal graft rejection episode and failure, dry eye syndrome (DES), Fuchs' dystrophy, corneal limbal stem cell deficiency, cataract, glaucoma, or other corneal condition. Operation 2506 may be performed by a subsystem that is the same as or similar to condition prediction subsystem 112, in accordance with one or more embodiments.

In some embodiments, the various computers and subsystems illustrated in FIG. 1A may include one or more computing devices that are programmed to perform the functions described herein. The computing devices may include one or more electronic storages (e.g., prediction database(s) 132, which may include training data database(s) 134, model database(s) 136, etc., or other electric storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other technologies). The computing devices may include a plurality of hardware, software, and/or firmware components operating together. For example, the computing devices may be implemented by a cloud of computing platforms operating together as the computing devices.

The electronic storages may include non-transitory storage media that electronically stores information. The electronic storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

The processors may be programmed to provide information processing capabilities in the computing devices. As such, the processors may include one or more of a digital processor, an analog processor, a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-114 or other subsystems. The processors may be programmed to execute computer program instructions by software; hardware; firmware; some combination of software, hardware, or firmware; and/ or other mechanisms for configuring processing capabilities on the processors.

It should be appreciated that the description of the functionality provided by the different subsystems 112-114 described herein is for illustrative purposes, and is not intended to be limiting, as any of subsystems 112-114 may provide more or less functionality than is described. For example, one or more of subsystems 112-114 may be eliminated, and some or all of its functionality may be provided by other ones of subsystems 112-114. As another example, additional subsystems may be programmed to perform some or all of the functionality attributed herein to one of subsystems 112-114.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

The present techniques will be better understood with reference to the following enumerated embodiments:

A1. A method comprising: providing a set of eye images related to a subject to a model; and obtaining, via the model, one or more predictions related to at least one eye condition for the subject, the model generating the one or more predictions based on the set of eye images.

A2. The method of embodiment A1, wherein the model is configured to: (i) take, as input, eye images; (ii) obtain a first prediction related to an eye condition, (iii) obtain a second prediction related to the eye condition; and (iv) adjust an aspect associated with the first prediction based on an aspect associated with the second prediction, wherein the first prediction is derived from a first eye image of the eye images, and the second prediction is derived from a second eye image of the eye images.

A3. The method of embodiment A2, wherein the model comprises a neural network, and the neural network comprises: at least one input layer configured to take, as input, the eye images; and at least one hidden layer configured to (i) obtain the first prediction derived from the first eye image, (ii) obtain the second prediction derived from the second eye image; and (iii) adjust the aspect associated with the first prediction based on the aspect associated with the second prediction.

A4. The method of any of embodiments A2-A3, wherein each of the eye images represents a different eye portion of an eye of the subject from one another, and wherein the aspects associated with the first and second predictions respectively comprises a weight or probability associated with the first prediction and an eye location associated with the second prediction such that the model is configured to perform the adjustment by adjusting the weight or probability associated with the first prediction based on the eye location associated with the second prediction, the eye location associated with the second prediction being a location of the eye that corresponds to the eye portion represented by the second eye image.

A5. The method of embodiment A4, wherein the model is configured to adjust the weight or probability associated with the first prediction based on a distance between (i) an eye location associated with the first prediction and (ii) the eye location associated with the second prediction, the eye location associated with the first prediction being a location of the eye that corresponds to the eye portion represented by the first eye image.

A6. The method of embodiment A5, wherein the model is configured to adjust the weight or probability associated with the first prediction based on distances between (i) the eye location associated with the first prediction and (ii) eye locations associated with other predictions derived from at least some of the eye images, the eye locations associated with the other predictions comprising the eye location associated with the second prediction.

A7. The method of embodiment A6, wherein the model is configured to perform the adjustment by increasing the weight or probability associated with the first prediction based on the eye location associated with the first prediction being close in proximity to the other eye locations associated with the other predictions.

A8. The method of embodiment A7, wherein the model is configured to perform the adjustment by increasing the weight or probability associated with the first prediction based on (i) the first prediction indicating that the eye condition is present in an eye of the subject, (ii) each of the other predictions indicating that the eye condition is present in the eye of the subject, and (iii) the eye location associated with the first prediction being close in proximity to the other eye locations associated with the other predictions.

A9. The method of any of embodiments A2-A8, wherein the model is configured to perform the adjustment by adjusting the aspect associated with the first prediction based on the second prediction indicating that the eye condition is present in an eye of the subject.

A10. The method of any of embodiments A2-A9, wherein the model is configured to take, as input, the eye images and one or more thickness maps, and wherein the model is configured to generate the first and second predictions based on the eye images and the one or more thickness maps.

A11. The method of any of embodiments A1-A10, further comprising: providing an initial set of eye images related to the subject to the second model to obtain the set of eye images from the second model, the set of eye images comprising versions of eye images of the initial set that are aligned by the second model; and providing the aligned versions to the model such that the model generates the one or more predictions based on the aligned versions.

A12. The method of any of embodiments A1-A11, further comprising: providing multiple frames of a same image cut from an eye scan to the model to train the model, the model generating at least one prediction related to at least one eye condition based on the multiple frames of the same image cut.

A13. The method of embodiment A12, wherein providing the multiple frames comprises providing multiple raw frames of the same image cut from the eye scan to the model such that each frame of the multiple raw frames of the same image cut comprises different noise patterns from other frames of the multiple raw frames.

A14. The method of any of embodiments A1-A13, further comprising: providing multiple raw frames of a first image cut from a first eye scan and multiple raw frames of a second image cut from a second eye scan to the model to obtain the one or more predictions, wherein the model generates the one or more predictions based on the multiple raw frames of the first and second image cuts.

A15. The method of any of embodiments A1-A14, wherein the one or more predictions relate to at least one of corneal ectasia, Keratoconus, corneal graft rejection episode and failure, dry eye syndrome (DES), Fuchs' dystrophy, corneal limbal stem cell deficiency, cataract, or glaucoma.

B1. A tangible, non-transitory, machine-readable medium storing instructions that, when executed by a data processing apparatus, cause the data processing apparatus to perform operations comprising those of any of embodiments A1-A15.

B2. A system comprising: one or more processors; and memory storing instructions that, when executed by the processors, cause the processors to effectuate operations comprising those of any of embodiments A1-A15.

What is claimed is:

1. A system for facilitating neural-network-based determinations of eye-related conditions, the system comprising:
   a neural network comprising a plurality of layers, the plurality of layers comprising:
   at least one input layer configured to take, as input, eye images; and
   at least one hidden layer configured to (i) obtain a first prediction related to an eye condition, (ii) obtain a second prediction related to the eye condition, and (iii) adjust a weight or probability associated with the first prediction based on a distance between a first eye location associated with the first prediction and a second eye location associated with the second prediction, wherein the at least one hidden layer is configured to perform the adjustment by increasing the weight or probability associated with the first prediction based on the distance between the first eye location and the second eye location, wherein the first prediction is derived from a first eye image of the eye images, and the second prediction is derived from a second eye image of the eye images, and wherein the first eye location and the second eye location are locations that correspond to eye portions represented by the first eye image and the second eye image, respectively; and one or more processors executing computer program instructions that, when executed, cause the one or more processors to:

provide a set of eye images related to a subject to the neural network; and obtain, via the neural network, one or more predictions related to at least one eye condition for the subject, the neural network generating the one or more predictions based on the set of eye images.

2. The system of claim 1, further comprising:
a second neural network configured to perform alignment of eye images,
wherein the one or more processors are caused to:
provide an initial set of eye images related to the subject to the second neural network to obtain the set of eye images from the second neural network, the set of eye images comprising versions of eye images of the initial set that are aligned by the second neural network,
wherein providing the set of eye images to the neural network comprises providing the aligned versions to the neural network such that the neural network generates the one or more predictions based on the aligned versions.

3. The system of claim 1, wherein each of the eye images represents a different eye portion of an eye of the subject from one another.

4. The system of claim 1, wherein the at least one hidden layer is configured to adjust perform the adjustment by increasing the weight or probability associated with the first prediction based on distances between (i) the first eye location associated with the first prediction and (ii) eye locations associated with other predictions derived from at least some of the eye images, the eye locations associated with the other predictions comprising the second eye location associated with the second prediction.

5. The system of claim 4, wherein the at least one hidden layer is configured to perform the adjustment by increasing the weight or probability associated with the first prediction based on the first eye location associated with the first prediction being close in proximity to the other eye locations associated with the other predictions.

6. The system of claim 5, wherein the at least one hidden layer is configured to perform the adjustment by increasing the weight or probability associated with the first prediction based on (i) the first prediction indicating that the eye condition is present in an eye of the subject, (ii) each of the other predictions indicating that the eye condition is present in an eye of the subject, and (iii) the first eye location associated with the first prediction being close in proximity to the other eye locations associated with the other predictions.

7. The system of claim 1, wherein the at least one hidden layer is configured to perform the adjustment by adjusting the weight or probability associated with the first prediction further based on the second prediction indicating that the eye condition is present in an eye of the subject.

8. The system of claim 1, wherein the at least one input layer is configured to take, as input, the eye images and one or more thickness maps, and wherein the neural network is configured to generate the first and second predictions based on the eye images and the one or more thickness maps.

9. The system of claim 1, wherein the one or more processors are caused to:
provide multiple frames of a same image cut from an eye scan to the neural network to train the neural network, the neural network generating at least one prediction related to at least one eye condition based on the multiple frames of the same image cut.

10. The system of claim 9, wherein providing the multiple frames comprises providing multiple raw frames of the same image cut from the eye scan to the neural network such that each frame of the multiple raw frames of the same image cut comprises different noise patterns from other frames of the multiple raw frames.

11. The system of claim 1, wherein the one or more processors are caused to:
provide multiple frames of a first image cut from a first eye scan and multiple frames of a second image cut from a second eye scan to the neural network to obtain the one or more predictions,
wherein the neural network generates the one or more predictions based on the multiple frames of the first and second image cuts.

12. The system of claim 1, wherein the one or more predictions relate to at least one of eye ectasia, Keratoconus, corneal graft rejection episode and failure, dry eye syndrome (DES), Fuchs' dystrophy, corneal limbal stem cell deficiency, cataract, or glaucoma.

13. The system of claim 1, wherein the one or more predictions relate to two or more of corneal ectasia, Keratoconus, corneal graft rejection episode and failure, dry eye syndrome (DES), Fuchs' dystrophy, corneal limbal stem cell deficiency, cataract, or glaucoma.

14. A method implemented by one or more processors executing computer program instructions that, when executed, perform the method, the method comprising:
providing a set of eye images related to a subject to a prediction model;
obtaining, via the prediction model, a first prediction indicating whether an eye condition is present in the subject, the first prediction being derived from a first eye image of the eye images;
obtaining, via the prediction model, a second prediction indicating that the eye condition is present in the subject, the second prediction being derived from a second eye image of the eye images;
adjusting, via the prediction model, a weight or probability associated with the first prediction based on a distance between a first eye location associated with the first prediction and a second eye location associated with the second prediction,
wherein adjusting the weight or probability comprises increasing the weight or probability associated with the first prediction based on the distance between the first eye location and the second eye location, wherein the first eye location and the second eye location are locations that correspond to eye portions represented by the first eye image and the second eye image, respectively; and obtaining, from the prediction model, one or more predictions related to at least one eye condition for the subject, the prediction model generating the one or more predictions based on the adjustment of the first prediction.

15. The method of claim 14, wherein each eye image of the set of eye images represents a different eye portion of an eye of the subject from one another.

16. The method of claim 14, wherein adjusting the weight or probability associated with the first prediction comprises adjusting the weight or probability associated with the first prediction based on the second prediction indicating that the eye condition is present in an eye of the subject.

17. The method of claim 14, further comprising:

providing multiple frames of a first image cut from a first eye scan and multiple frames of a second image cut from a second eye scan to the prediction model to obtain the one or more predictions, wherein the prediction model generates the first prediction based on the multiple frames of the first image cut, and wherein the prediction model generates the second prediction based on the multiple frames of the second image cut.

18. Non-transitory computer-readable media comprising computer program instructions that, when executed by one or more processors, perform operations comprising:

providing a set of eye images related to a subject to a prediction model;

obtaining, via the prediction model, a first prediction indicating whether an eye condition is present in the subject, the first prediction being derived from a first eye image of the eye images;

obtaining, via the prediction model, a second prediction indicating that the eye condition is present in the subject, the second prediction being derived from a second eye image of the eye images;

adjusting, via the prediction model, a weight or probability associated with the first prediction based on a distance between a first eye location associated with the first prediction and a second eye location associated with the second prediction, wherein adjusting the weight or probability comprises increasing the weight or probability associated with the first prediction based on the distance between the first eye location and the second eye location, wherein the first eye location and the second eye location are locations that correspond to eye portions represented by the first eye image and the second eye image, respectively; and obtaining, from the prediction model, one or more predictions related to at least one eye condition for the subject, the prediction model generating the one or more predictions based on the adjustment of the first prediction.

* * * * *